(12) United States Patent
Nagasaka et al.

(10) Patent No.: US 10,725,127 B2
(45) Date of Patent: *Jul. 28, 2020

(54) MAGNETIC FIELD MEASUREMENT METHOD AND MAGNETIC FIELD MEASUREMENT APPARATUS

(71) Applicant: SEIKO EPSON CORPORATION, Tokyo (JP)

(72) Inventors: Kimio Nagasaka, Hokuto (JP); Mitsutoshi Miyasaka, Suwa (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/260,510

(22) Filed: Jan. 29, 2019

(65) Prior Publication Data

US 2019/0154769 A1 May 23, 2019

Related U.S. Application Data

(63) Continuation of application No. 14/955,732, filed on Dec. 1, 2015, now Pat. No. 10,254,356.

(30) Foreign Application Priority Data

Dec. 2, 2014 (JP) .................................. 2014-243867
Aug. 11, 2015 (JP) .................................. 2015-158756

(51) Int. Cl.
*G01R 33/26* (2006.01)
*A61B 5/04* (2006.01)
*G01R 33/032* (2006.01)

(52) U.S. Cl.
CPC .......... *G01R 33/26* (2013.01); *A61B 5/04005* (2013.01); *G01R 33/0322* (2013.01); *A61B 5/04007* (2013.01); *A61B 5/04008* (2013.01)

(58) Field of Classification Search
CPC ................................................... G01R 33/26; G01R 33/0322; A61B 5/04005; A61B 5/04007; A61B 5/04008
(Continued)

(56) References Cited

U.S. PATENT DOCUMENTS 6,528,993 B1  3/2003  Shin et al.
2007/0120563 A1* 5/2007 Kawabata .......... G01R 33/0354
                                                      324/244.1

FOREIGN PATENT DOCUMENTS

JP   2013-108833 A   6/2013
WO   2004/051299 A2  6/2004

OTHER PUBLICATIONS

Seltzer et al. "Unshielded Three-Axis Vector Operation of a Spin-Exchange-Relaxation-Free Atomic Magnetometer". Applied Physics Letters, vol. 85, No. 20, pp. 4804-4806, Nov. 15, 2004.
(Continued)

*Primary Examiner* — Melissa J Koval
*Assistant Examiner* — Rahul Maini
(74) *Attorney, Agent, or Firm* — Oliff PLC

(57) ABSTRACT

In a magnetic field measurement apparatus, a light source irradiates a gas cell with linearly polarized light serving as pump light and probe light in a Z axis direction, and a magnetic field generator applies, to the gas cell, a magnetic field $A_x$ which is a time function f(t) having the amplitude $A_0$ taking n fixed values $f_i$ (where i=1, ..., and n), and a magnetic field $A_y$ which is a time function g(t) having the amplitude $A_0$ taking m fixed values $g_j$ (where j=1, ..., and m) in each of X axis and Y axis directions. A calculation controller calculates a magnetic field C ($C_x$, $C_y$, $C_z$) of a measurement region using the X axis and Y axis components $A_x$ and $A_y$ of an artificial magnetic field A, and a spin polarization degree $M_x$ corresponding to a measurement value $W_-$ from a magnetic sensor.

1 Claim, 15 Drawing Sheets

(58) Field of Classification Search
USPC .......................................................... 324/304
See application file for complete search history.

(56) References Cited

OTHER PUBLICATIONS

Fang, J. et al. "In Situ Triaxial Magnetic Field Compensation for the Spin-Exchange-Relaxation-Free Atomic Magnetometer". Review of Scientific Instruments, vol. 83, pp. 103104-1-103104-7, 2012.
Taue, S. et al. "Magnetic Field Mapping and Biaxial Vector Operation for Biomagnetic Applications Using High-Sensitivity Optically Pumped Atomic Magnetometers". Japanese Journal of Applied Physics, vol. 50, pp. 116604-1-116604-6, 2011.
May 6, 2016 Extended Search Report issued in European Patent Application No. 15197517.4.
Sep. 11, 2018 Office Action issued in U.S. Appl. No. 14/955,732.
Nov. 28, 2018 Notice of Allowance issued in U.S. Appl. No. 14/955,732.

* cited by examiner

MAGNETIC FIELD MEASUREMENT METHOD AND MAGNETIC FIELD MEASUREMENT APPARATUS

CROSS-REFERENCE TO RELATED APPLICATION(S)

This application is a divisional of U.S. application Ser. No. 14/955,732 filed Dec. 1, 2015, which is based on and claims priority under 35 U.S.C. 119 from Japanese Patent Application No. 2014-243867 filed on Dec. 2, 2014 and Japanese Patent Application No. 2015-158756 filed on Aug. 11, 2015. The contents of the above applications are incorporated by reference in their entireties.

BACKGROUND

1. Technical Field

The present invention relates to a magnetic field measurement method using light and a magnetic field measurement apparatus.

2. Related Art

A magnetic field measurement apparatus using light can measure a weak magnetic field generated from a living body, such as a magnetic field (heart magnetic field) from the heart or a magnetic field (brain magnetic field) from the brain, and is expected to be applied to a medical image diagnostic apparatus or the like. In such a magnetic field measurement apparatus, pump light and probe light are applied to a gas cell in which gaseous alkali metals or the like are sealed. Atoms enclosed in the gas cell are excited by the pump light so as to be spin-polarized, and a polarization plane of the probe light which is transmitted through the gas cell is rotated according to a magnetic field due to the magneto-optical effect. A magnetic field is measured by measuring rotation angles of the polarization plane of the probe light before and after being transmitted through the gas cell (for example, JP-A-2013-108833).

In a general magnetic field measurement apparatus using an optical pumping method of the related art, a detection axis of a magnetic field is located in the same direction, and if directions of the detection axis and the magnetic field are different from each other, a projection component of the magnetic field onto the detection axis is measured. However, a magnetic field which is actually distributed in a space is expressed as three-dimensional vectors, and if a magnetic field is to be measured more accurately, magnetic fields in three-axis directions such as three orthogonal XYZ axes are preferably measured. Since a detection axis is located in a direction corresponding to an irradiation direction of probe light, it is necessary to cause the respective irradiation directions to be accurately perpendicular to each other in a case where the detection axes are increased by simply increasing the irradiation directions of the probe light. If an irradiation direction is tilted with respect to an expected direction, a detection axis is thus also tilted, and, as a result, errors occur in a measured value of a magnetic field which is expressed as three-dimensional vectors.

SUMMARY

An advantage of some aspects of the invention is that magnetic fields in a plurality of directions can be measured while applying probe light in one direction, or a magnetic field can be measured with high accuracy in magnetic field measurement using an optical pumping method.

Application Example 1

Application Example 1 is directed to a magnetic field measurement method of measuring a magnetic field of a measurement region in a magnetic field measurement apparatus in which a first direction, a second direction, and a third direction are perpendicular to each other and which includes a light source that emits light, a medium through which the light passes in the third direction and that changes optical characteristics depending on a magnetic field of the measurement region, a photodetector that detects the optical characteristics, and a first magnetic field generator that applies a magnetic field in the first direction to the measurement region. The method includes causing the first magnetic field generator to generate a constant magnetic field with a first level on the first direction side, a constant magnetic field with a second level on the first direction side, and a constant magnetic field with a third level on the first direction side, as the magnetic field in the first direction; and calculating the magnetic field of the measurement region using a detection result from the photodetector and the magnetic field in the first direction.

In the magnetic field measurement method of this application example, it is possible to calculate a magnetic field vector of the measurement region through irradiation with light in only one direction such as the third direction (Z direction). In other words, it is possible to calculate a first direction (X direction) component, a second direction (Y direction) component, and a third direction (Z direction) component of the magnetic field of the measurement region through irradiation with light in only one direction. Specifically, as the magnetic field in the first direction (X direction) perpendicular to the third direction (Z direction) which is an irradiation direction of the light, the constant magnetic fields with three levels are applied to the medium which changes optical characteristics of the light according to a magnetic field of the measurement region. The magnetic field of the measurement region is calculated using a detection result of the optical characteristics of the light, and the magnetic field in the first direction (X direction).

Application Example 2

As Application Example 2, the magnetic field measurement method according to Application Example 1 may be configured such that, in the calculating of the magnetic field of the measurement region, a magnetization value indicating a component in the first direction of a magnetization vector of the medium is calculated on the basis of the detection result from the photodetector, and the magnetic field of the measurement region is calculated using a (1-1)-th magnetization value obtained when the constant magnetic field with the first level on the first direction side is generated, a (2-1)-th magnetization value obtained when the constant magnetic field with the second level on the first direction side is generated, a (3-1)-th magnetization value obtained when the constant magnetic field with the third level on the first direction side is generated, and the magnetic field in the first direction.

In the magnetic field measurement method of this application example, a magnetization value indicating a first direction (X direction) component of a magnetization vector of the medium is calculated on the basis of a detection result of the optical characteristics in the medium, and a magnetic field vector (a first direction (X direction) component, a second direction (Y direction) component, and a third direction (Z direction)component of the magnetic field) of the measurement region is calculated using three magnetization values respectively obtained when the constant magnetic fields with the three levels are generated as the magnetic field in the first direction (X direction), and the magnetic field in the first direction (X direction).

Application Example 3

As Application Example 3, the magnetic field measurement method according to Application Example 2 may be configured such that, in the calculating of the magnetic field of the measurement region, the following Equation 1 is applied to combinations of a constant magnetic field with an i-th level (where i=1, 2, and 3) on the first direction side, which is the magnetic field in the first direction, and a magnetization value obtained when the magnetic field in the first direction is generated.

$$M_{xi} = \frac{c}{a} \cdot \frac{C_x C_y + C_y A_{10} f_i + a C_z}{a^2 + C_x^2 + C_y^2 + C_z^2 + 2C_x A_{10} f_i + (A_{10} f_i)^2} \quad (1)$$

In the equation, the magnetic field of the measurement region is expressed by $C=(C_x, C_y, C_z)$; x, y, and z respectively indicate spatial coordinates in the first direction, the second direction, and the third direction; $M_{xi}$ indicates the magnetization value obtained when the constant magnetic field with the i-th level on the first direction side is generated; a and c are constants; and $A_{10} f_i$ indicates the constant magnetic field with the i-th level on the first direction side.

In the magnetic field measurement method of this application example, the magnetic field $(C_x, C_y, C_z)$ of the measurement region of the medium, which is a three-dimensional vector, can be calculated by solving simultaneous equations, the simultaneous equations being defined by three equations obtained by assigning respective values of combinations of the constant magnetic fields with three levels as the magnetic field in the first direction (X direction) and the magnetization values obtained when the constant magnetic fields are generated, to Equation 1.

Application Example 4

As Application Example 4, the magnetic field measurement method according to anyone of Application Examples 1 to 3 may be configured such that at least one of the constant magnetic field with the first level on the first direction side, the constant magnetic field with the second level on the first direction side, and the constant magnetic field with the third level on the first direction side is a zero magnetic field.

Application Example 5

Application Example 5 is directed to a magnetic field measurement method of measuring a magnetic field of a measurement region in a magnetic field measurement apparatus in which a first direction, a second direction, and a third direction are perpendicular to each other and which includes a light source that emits light, a medium through which the light passes in the third direction and that changes optical characteristics depending on a magnetic field of the measurement region, a photodetector that detects the optical characteristics, and a second magnetic field generator that applies a magnetic field in the second direction to the measurement region. The method includes causing the second magnetic field generator to generate a constant magnetic field with a first level on the second direction side, a constant magnetic field with a second level on the second direction side, and a constant magnetic field with a third level on the second direction side, as the magnetic field in the second direction; and calculating the magnetic field of the measurement region using a detection result from the photodetector and the magnetic field in the second direction.

In the magnetic field measurement method of this application example, it is possible to calculate a magnetic field vector of the measurement region through irradiation with light only in one direction such as the third direction (Z direction). In other words, it is possible to calculate a first direction (X direction) component, a second direction (Y direction) component, and a third direction (Z direction) component of the magnetic field of the measurement region through irradiation with light only in one direction. Specifically, as the magnetic field in the second direction (Y direction) perpendicular to the third direction (Z direction) which is an irradiation direction of the light, the constant magnetic fields with three levels are applied to the medium which changes optical characteristics of the light according to a magnetic field of the measurement region. The magnetic field of the measurement region is calculated using a detection result of the optical characteristics of the light, and the magnetic field in the second direction (Y direction).

Application Example 6

As Application Example 6, the magnetic field measurement method according to Application Example 5 may be configured such that, in the calculating of the magnetic field of the measurement region, a magnetization value indicating a component in the first direction of a magnetization vector of the medium is calculated on the basis of the detection result from the photodetector, and the magnetic field of the measurement region is calculated using a (1-1)-th magnetization value obtained when the constant magnetic field with the first level on the second direction side is generated, a (1-2)-th magnetization value obtained when the constant magnetic field with the second level on the second direction side is generated, a (1-3)-th magnetization value obtained when the constant magnetic field with the third level on the second direction side is generated, and the magnetic field in the second direction.

In the magnetic field measurement method of this application example, a magnetization value indicating a first direction (X direction) component of a magnetization vector of the medium is calculated on the basis of a detection result of the optical characteristics in the medium, and a magnetic field vector (a first direction (X direction) component, a second direction (Y direction) component, and a third direction (Z direction) component of the magnetic field) of the measurement region is calculated using three magnetization values respectively obtained when the constant magnetic fields with the three levels are generated as the magnetic field in the second direction (Y direction), and the magnetic field in the second direction (Y direction).

Application Example 7

As Application Example 7, the magnetic field measurement method according to Application Example 6 may be configured such that, in the calculating of the magnetic field of the measurement region, the following Equation 2 is applied to combinations of a constant magnetic field with a j-th level (where j=1, 2, and 3) on the second direction side, which is the magnetic field in the second direction, and a magnetization value obtained when the magnetic field in the second direction is generated.

$$M_{xj} = \frac{c}{a} \cdot \frac{C_x C_y + C_x A_{20} g_j + a C_z}{a^2 + C_x^2 + C_y^2 + C_z^2 + 2 C_y A_{20} g_j + (A_{20} g_j)^2} \quad (2)$$

In the equation, the magnetic field of the measurement region is expressed by $C=(C_x, C_y, C_z)$; x, y, and z respectively indicate spatial coordinates in the first direction, the second direction, and the third direction; $M_{xj}$ indicates the magnetization value obtained when the constant magnetic field with the j-th level on the second direction side is generated; a and c are constants; and $A_{20} g_j$ indicates the constant magnetic field with the j-th level on the second direction side.

In the magnetic field measurement method of this application example, the magnetic field ($C_x$, $C_y$, $C_z$) of the measurement region of the medium, which is a three-dimensional vector, can be calculated by solving simultaneous equations, the simultaneous equations being defined by three equations obtained by assigning respective values of combinations of the constant magnetic fields with three levels as the magnetic field in the second direction (Y direction) and the magnetization values obtained when the constant magnetic fields are generated, to Equation 2.

Application Example 8

As Application Example 8, the magnetic field measurement method according to anyone of Application Examples 5 to 7 may be configured such that at least one of the constant magnetic field with the first level on the second direction side, the constant magnetic field with the second level on the second direction side, and the constant magnetic field with the third level on the second direction side is a zero magnetic field.

Application Example 9

Application Example 9 is directed to a magnetic field measurement method of measuring a magnetic field of a measurement region in a magnetic field measurement apparatus in which a first direction, a second direction, and a third direction are perpendicular to each other and which includes a light source that emits light, a medium through which the light passes in the third direction and that changes optical characteristics depending on a magnetic field of the measurement region, a photodetector that detects the optical characteristics, a first magnetic field generator that applies a magnetic field in the first direction to the measurement region, and a second magnetic field generator that applies a magnetic field in the second direction to the measurement region. The method includes causing the first magnetic field generator to generate a constant magnetic field with a first level on the first direction side and a constant magnetic field with a second level on the first direction side as the magnetic field in the first direction; causing the second magnetic field generator to generate a constant magnetic field with a first level on the second direction side and a constant magnetic field with a second level on the second direction side as the magnetic field in the second direction; and calculating the magnetic field of the measurement region using a detection result from the photodetector, the magnetic field in the first direction, and the magnetic field in the second direction.

In the magnetic field measurement method of this application example, it is possible to calculate a magnetic field vector of the measurement region through irradiation with light in only one direction such as the third direction (Z direction). Specifically, as the magnetic field in the first direction (X direction) perpendicular to the third direction (Z direction) which is an irradiation direction of the light, the constant magnetic fields with two levels are applied to the medium which changes optical characteristics of the light according to a magnetic field of the measurement region, and as the magnetic field in the second direction (Y direction) perpendicular to the third direction (Z direction) and the first direction (X direction), the constant magnetic fields with two levels are applied thereto. The magnetic field of the measurement region is calculated using a detection result of the optical characteristics of the light, the magnetic field in the first direction (X direction), and the magnetic field in the second direction (Y direction).

Application Example 10

As Application Example 10, the magnetic field measurement method according to Application Example 9 may be configured such that, in the calculating of the magnetic field of the measurement region, a magnetization value indicating a component in the first direction of a magnetization vector of the medium is calculated on the basis of the detection result from the photodetector, and the magnetic field of the measurement region is calculated using 1) three or more magnetization values among a (1-1)-th magnetization value obtained when the constant magnetic field with the first level on the first direction side and the constant magnetic field with the first level on the second direction side are generated, a (1-2)-th magnetization value obtained when the constant magnetic field with the first level on the first direction side and the constant magnetic field with the second level on the second direction side are generated, a (2-1)-th magnetization value obtained when the constant magnetic field with the second level on the first direction side and the constant magnetic field with the first level on the second direction side are generated, and a (2-2)-th magnetization value obtained when the constant magnetic field with the second level on the first direction side and the constant magnetic field with the second level on the second direction side are generated; 2) the magnetic field in the first direction; and 3) the magnetic field in the second direction.

In the magnetic field measurement method of this application example, a magnetization value indicating a first direction (X direction) component of a magnetization vector of the medium is calculated on the basis of a detection result of the optical characteristics in the medium, and a magnetic field of the measurement region is calculated using three or more magnetization values among four magnetization values respectively obtained when the constant magnetic fields with the two levels are generated as the magnetic field in the first direction (X direction) and the constant magnetic fields with the two levels are generated as the magnetic field in the second direction (Y direction), the magnetic field in the first direction (X direction), and the magnetic field in the second direction (Y direction).

Application Example 11

As Application Example 11, the magnetic field measurement method according to Application Example 10 may be configured such that the calculating of the magnetic field of the measurement region is performed on the basis of the following Equation 3 being satisfied by each of combinations of a constant magnetic field with an i-th level (where i=1 and 2) on the first direction side, which is the magnetic field in the first direction, a constant magnetic field with a j-th level (where j=1 and 2) on the second direction side, which is the magnetic field in the second direction, and a magnetization value obtained when the magnetic field in the first direction and the magnetic field in the second direction are generated.

$$M_{xij} = \frac{c}{a} \cdot \frac{C_x C_y + C_x A_{20} g_j + C_y A_{10} f_i + A_{10} f_i A_{20} g_j + aC_z}{a^2 + C_x^2 + C_y^2 + C_z^2 + 2C_x A_{10} f_i + 2C_y A_{20} g_j + (A_{10} f_i)^2 + (A_{20} g_j)^2} \quad (3)$$

In the equation, the magnetic field of the measurement region is expressed by $C=(C_x, C_y, C_z)$; x, y, and z respectively indicate spatial coordinates in the first direction, the second direction, and the third direction; $M_{xij}$ indicates the magnetization value obtained when the constant magnetic field with the i-th level on the first direction side and the constant magnetic field with the j-th level on the second direction side are generated; a and c are constants; $A_{10} f_i$ indicates the constant magnetic field with the i-th level on the first direction side; and $A_{20} g_j$ indicates the constant magnetic field with the j-th level on the second direction side.

In the magnetic field measurement method of this application example, the magnetic field $(C_x, C_y, C_z)$ of the measurement region of the medium, which is a three-dimensional vector, can be calculated by solving simultaneous equations, the simultaneous equations being defined by four equations obtained by assigning respective values of combinations of the constant magnetic field with the i-th level on the X side as the magnetic field in the first direction (X direction), the constant magnetic field with the j-th level on the Y side as the magnetic field in the second direction (Y direction), and the magnetization values obtained when the magnetic field in the first direction (X direction) and the magnetic field in the second direction (Y direction) are generated, to Equation 3.

Application Example 12

As Application Example 12, the magnetic field measurement method according to anyone of Application Examples 9 to 11 maybe configured such that one of the constant magnetic field with the first level on the first direction side and the constant magnetic field with the second level on the first direction side is a zero magnetic field, and one of the constant magnetic field with the first level on the second direction side and the constant magnetic field with the second level on the second direction side is also a zero magnetic field.

Application Example 13

Application Example 13 is directed to a magnetic field measurement method of measuring a magnetic field of a measurement region in a magnetic field measurement apparatus in which a first direction, a second direction, and a third direction are perpendicular to each other and which includes a light source that emits light, a medium through which the light passes in the third direction and that changes optical characteristics depending on a magnetic field of the measurement region, a photodetector that detects the optical characteristics, a first magnetic field generator that applies a magnetic field in the first direction to the measurement region, a second magnetic field generator that applies a magnetic field in the second direction to the measurement region, and a third magnetic field generator that applies a magnetic field in the third direction to the measurement region. The method includes causing the first magnetic field generator to generate a constant magnetic field with a first level on the first direction side as the magnetic field in the first direction; a first procedure of calculating the magnetic field of the measurement region as an original magnetic field using a detection result from the photodetector and the magnetic field in the first direction; a second procedure of disposing a measurement target object in the measurement region; a third procedure of causing the first magnetic field generator, the second magnetic field generator, and the third magnetic field generator to generate a magnetic field corresponding to a difference between a target magnetic field which is desired to be formed in the measurement region and the original magnetic field; and a fourth procedure of measuring a magnetic field generated by the measurement target object using the detection result from the photodetector in a period in which the third procedure is being performed and the second procedure is completed.

In the magnetic field measurement method of this application example, a magnetic field generated by the measurement target object can be measured in a state in which a predetermined target magnetic field is formed in the measurement region. For example, if the target magnetic field is set to a zero magnetic field in order to cancel out the original magnetic field which enters the measurement region from the outside, it is possible to accurately measure the magnetic field generated by the measurement target object.

Application Example 14

Application Example 14 is directed to a magnetic field measurement method of measuring a magnetic field of a measurement region in a magnetic field measurement apparatus in which a first direction, a second direction, and a third direction are perpendicular to each other and which includes a light source that emits light, a medium through which the light passes in the third direction and that changes optical characteristics depending on a magnetic field of the measurement region, a photodetector that detects the optical characteristics, a first magnetic field generator that applies a magnetic field in the first direction to the measurement region, a second magnetic field generator that applies a magnetic field in the second direction to the measurement region, and a third magnetic field generator that applies a magnetic field in the third direction to the measurement region. The method includes causing the first magnetic field generator to generate a constant magnetic field with a first level on the first direction side as the magnetic field in the first direction; a first procedure of calculating the magnetic field of the measurement region as an original magnetic field using a detection result from the photodetector and the magnetic field in the first direction; a second procedure of disposing a measurement target object in the measurement region; a third procedure of causing the first magnetic field generator to generate a constant magnetic field in which a first direction component of a magnetic field corresponding to a difference between a target magnetic field which is desired to be formed in the measurement region and the original magnetic field is added to the constant magnetic field with the first level on the first direction side, causing the second magnetic field generator to generate a magnetic field having a second direction component of the magnetic field corresponding to the difference, and causing the third magnetic field generator to generate a magnetic field having a third direction component of the magnetic field corresponding to the difference; a fourth procedure of measuring a magnetic field generated by the measurement target object using the detection result from the photodetector and a constant magnetic field with a fourth level on the first direction side in a period in which the third procedure is being performed and the second procedure is completed.

In the magnetic field measurement method of this application example, a magnetic field generated by the measurement target object can be measured in a state in which a predetermined target magnetic field is formed in the measurement region. For example, if the target magnetic field is set to a zero magnetic field in order to cancel out the original magnetic field which enters the measurement region from the outside, it is possible to accurately measure the magnetic field generated by the measurement target object as a vector quantity.

Application Example 15

Application Example 15 is directed to a magnetic field measurement apparatus in which a first direction, a second direction, and a third direction are perpendicular to each other. The apparatus includes a light source that emits light; a medium through which the light passes in the third direction and that changes optical characteristics depending on a magnetic field of the measurement region; a photodetector that detects the optical characteristics; a first magnetic field generator that applies a magnetic field in the first direction to the measurement region; and a calculation controller that causes the first magnetic field generator to generate a constant magnetic field with a first level on the first direction side, a constant magnetic field with a second level on the first direction side, and a constant magnetic field with a third level on the first direction side, as the magnetic field in the first direction, and calculates the magnetic field of the measurement region using a detection result from the photodetector and the magnetic field in the first direction.

In the magnetic field measurement apparatus of this application example, it is possible to calculate a magnetic field vector of the measurement region through irradiation with light in only one direction such as the third direction (Z direction). In other words, it is possible to calculate a first direction (X direction) component, a second direction (Y direction) component, and a third direction (Z direction) component of the magnetic field of the measurement region through irradiation with light in only one direction. Specifically, as the magnetic field in the first direction (X direction) perpendicular to the third direction (Z direction) which is an irradiation direction of the light, the constant magnetic fields with three levels are applied to the medium which changes optical characteristics of the light according to a magnetic field of the measurement region. The magnetic field of the measurement region is calculated using a detection result of the optical characteristics of the light, and the magnetic field in the first direction (X direction).

Application Example 16

Application Example 16 is directed to a magnetic field measurement apparatus in which a first direction, a second direction, and a third direction are perpendicular to each other. The apparatus includes a light source that emits light; a medium through which the light passes in the third direction and that changes optical characteristics depending on a magnetic field of the measurement region; a photodetector that detects the optical characteristics; a second magnetic field generator that applies a magnetic field in the second direction to the measurement region; and a calculation controller that causes the second magnetic field generator to generate a constant magnetic field with a first level on the second direction side, a constant magnetic field with a second level on the second direction side, and a constant magnetic field with a third level on the second direction side, as the magnetic field in the second direction, and calculates the magnetic field of the measurement region using a detection result from the photodetector and the magnetic field in the second direction.

In the magnetic field measurement apparatus of this application example, it is possible to calculate a magnetic field vector of the measurement region through irradiation with light in only one direction such as the third direction (Z direction). In other words, it is possible to calculate a first direction (X direction) component, a second direction (Y direction) component, and a third direction (Z direction) component of the magnetic field of the measurement region through irradiation with light in only one direction. Specifically, as the magnetic field in the second direction (Y direction) perpendicular to the third direction (Z direction) which is an irradiation direction of the light, the constant magnetic fields with three levels are applied to the medium which changes optical characteristics of the light according to a magnetic field of the measurement region. The magnetic field of the measurement region is calculated using a detection result of the optical characteristics of the light, and the magnetic field in the second direction (Y direction).

Application Example 17

Application Example 17 is directed to a magnetic field measurement apparatus in which a first direction, a second direction, and a third direction are perpendicular to each other. The apparatus includes a light source that emits light; a medium through which the light passes in the third direction and that changes optical characteristics depending on a magnetic field of the measurement region; a photodetector that detects the optical characteristics; a first magnetic field generator that applies a magnetic field in the first direction to the measurement region; a second magnetic field generator that applies a magnetic field in the second direction to the measurement region; and a calculation controller that causes the first magnetic field generator to generate a constant magnetic field with a first level on the first direction side and a constant magnetic field with a second level on the first direction side as the magnetic field in the first direction, causes the second magnetic field generator to generate a constant magnetic field with a first level on the second direction side and a constant magnetic field with a second level on the second direction side as the magnetic field in the second direction, and calculates the magnetic field of the measurement region using a detection result from the photodetector, the magnetic field in the first direction, and the magnetic field in the second direction.

In the magnetic field measurement apparatus of this application example, it is possible to calculate a magnetic field vector of the measurement region through irradiation with light in only one direction such as the third direction (Z direction). Specifically, as the magnetic field in the first direction (X direction) perpendicular to the third direction (Z direction) which is an irradiation direction of the light, the constant magnetic fields with two levels are applied to the medium which changes optical characteristics of the light according to a magnetic field of the measurement region, and as the magnetic field in the second direction (Y direction) perpendicular to the third direction (Z direction) and the first direction (X direction), the constant magnetic fields with two levels are applied thereto. The magnetic field of the measurement region is calculated using a detection result of the optical characteristics of the light, the magnetic field in the first direction (X direction), and the magnetic field in the second direction (Y direction).

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
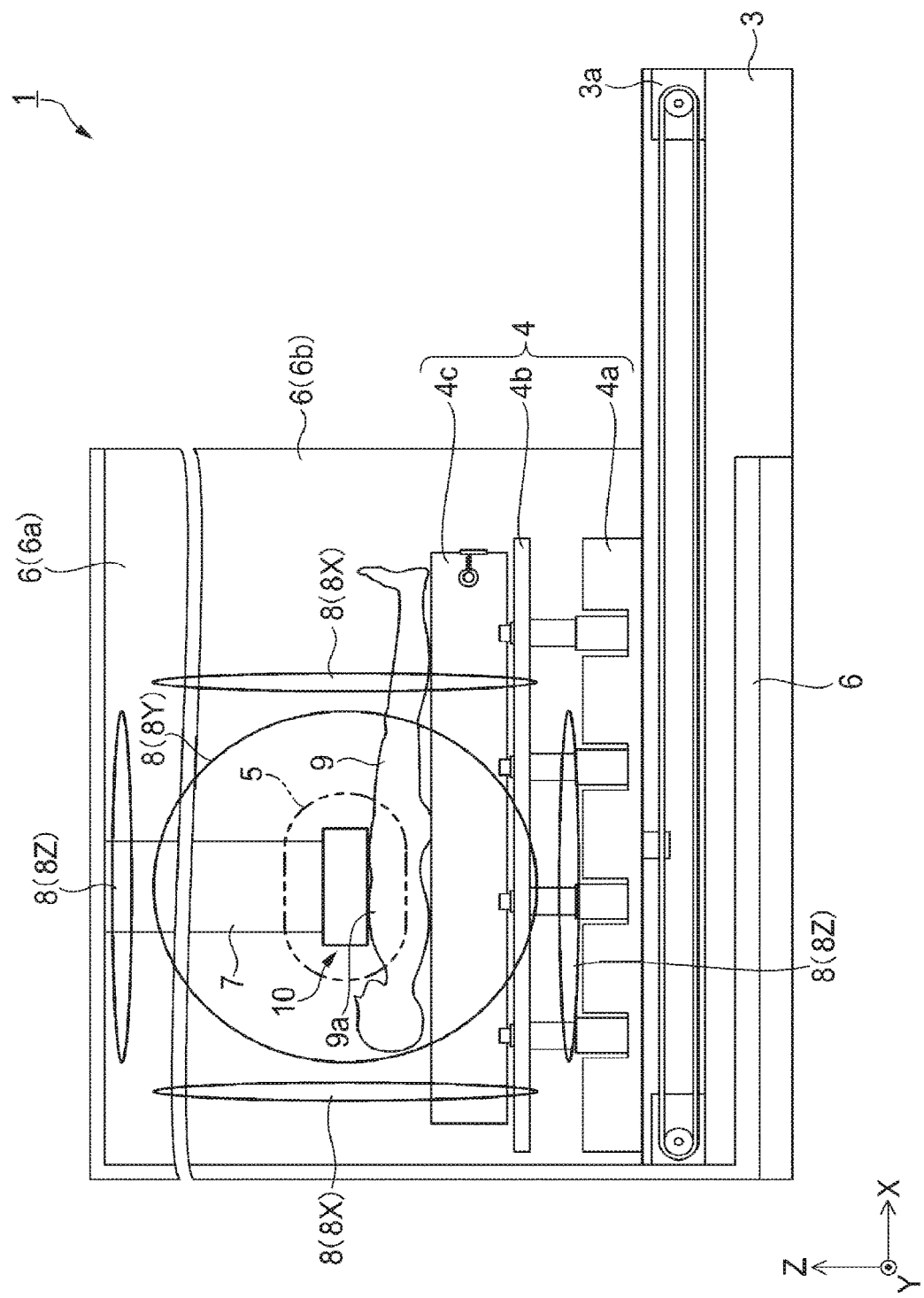
FIG. 1 is a schematic side view illustrating an example of a configuration of a magnetic field measurement apparatus according to the present embodiment.

Hereinafter, an embodiment will be described with reference to the drawings.

In addition, respective members in the drawings are illustrated in different scales in order to be recognizable in the drawings.

Configuration of Magnetic Field Measurement Apparatus

Figure 2:
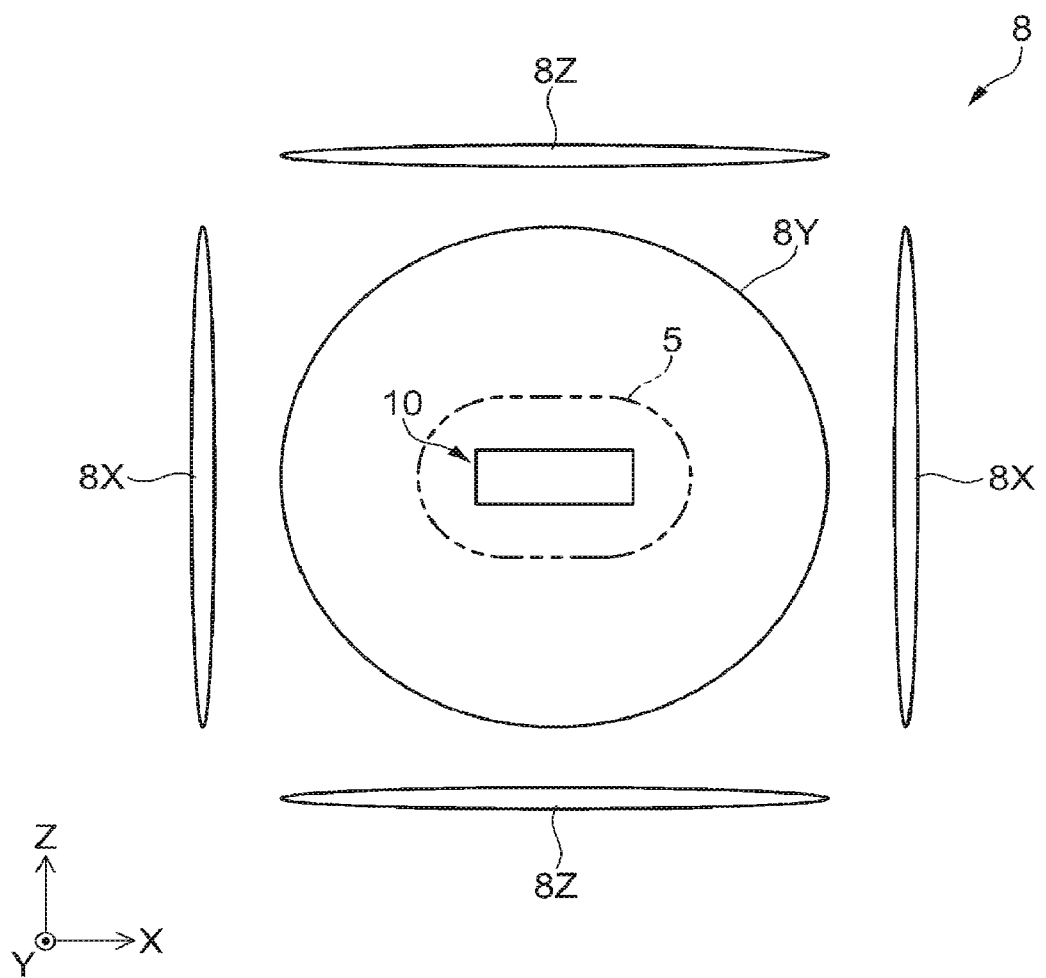
FIG. 2 is a schematic diagram illustrating a configuration of a magnetic field generator according to the present embodiment, and, specifically, is a diagram viewed from a Y direction.
Figure 3:
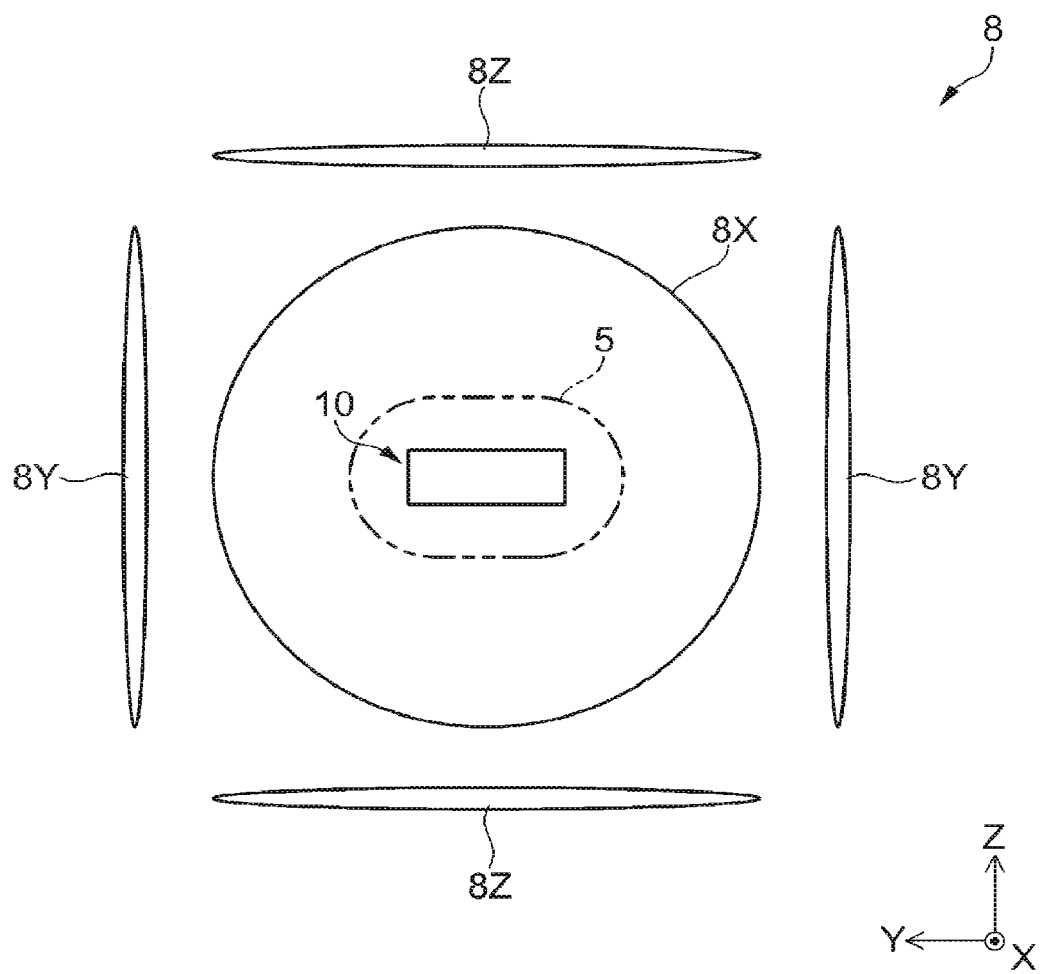
FIG. 3 is a schematic diagram illustrating the configuration of the magnetic field generator according to the present embodiment, and, specifically, is a diagram viewed from an X direction.
Figure 4:
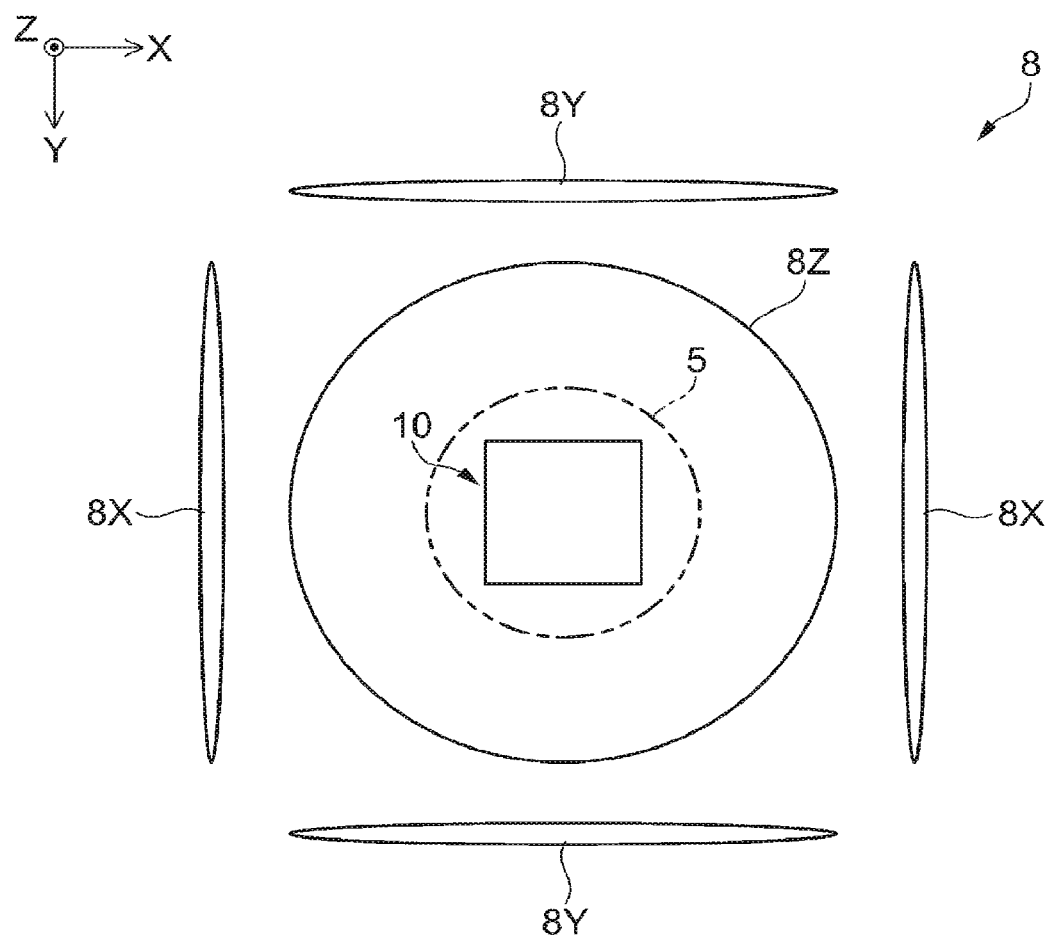
FIG. 4 is a schematic diagram illustrating the configuration of the magnetic field generator according to the present embodiment, and, specifically, is a diagram viewed from a Z direction.
Figure 5:
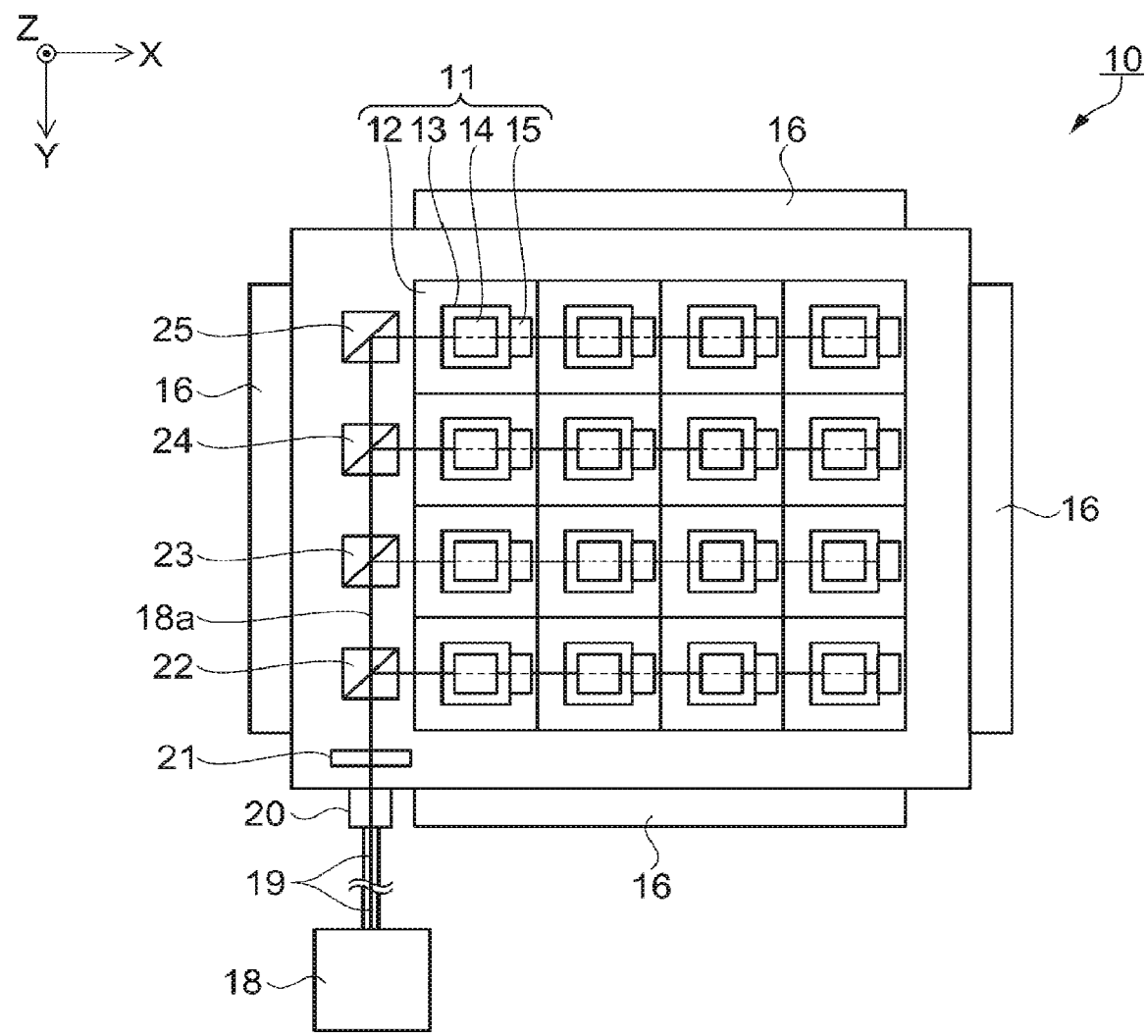
FIG. 5 is a schematic diagram illustrating a configuration of a magnetic sensor according to the present embodiment, and, specifically, is a plan view viewed from the Z direction.
Figure 6:
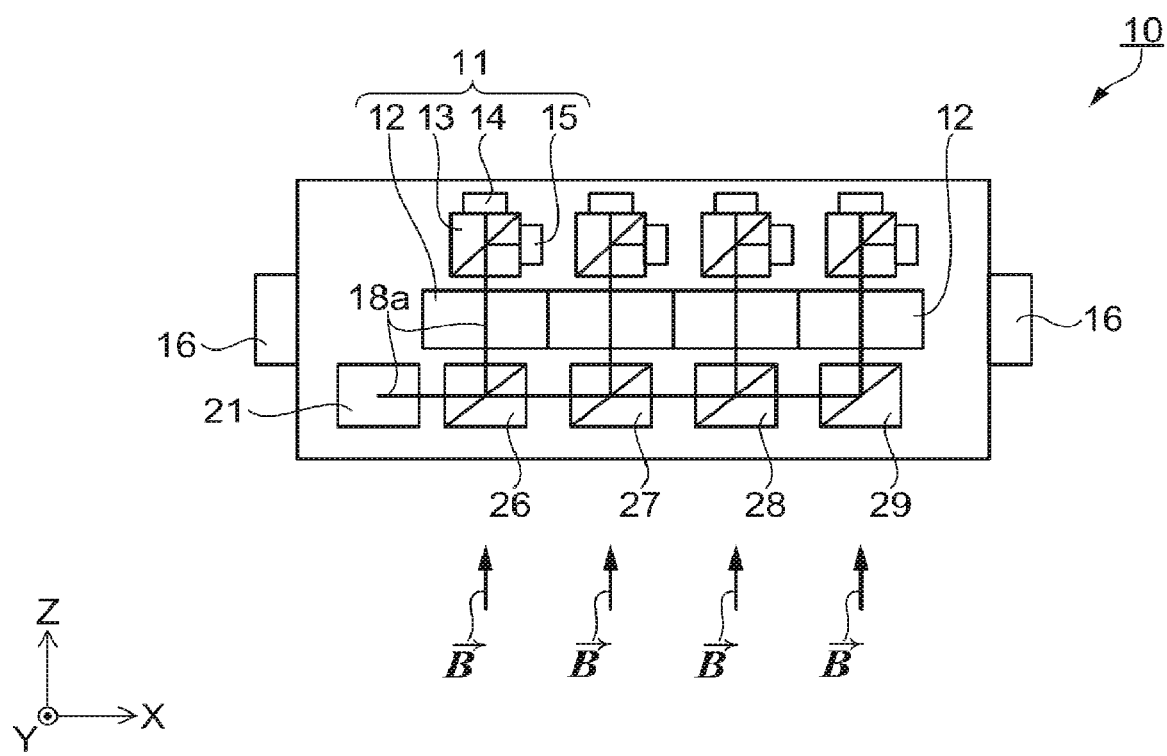
FIG. 6 is a schematic diagram illustrating the configuration of the magnetic sensor according to the present embodiment, and, specifically, is a side view viewed from the Y direction.
Figure 7:
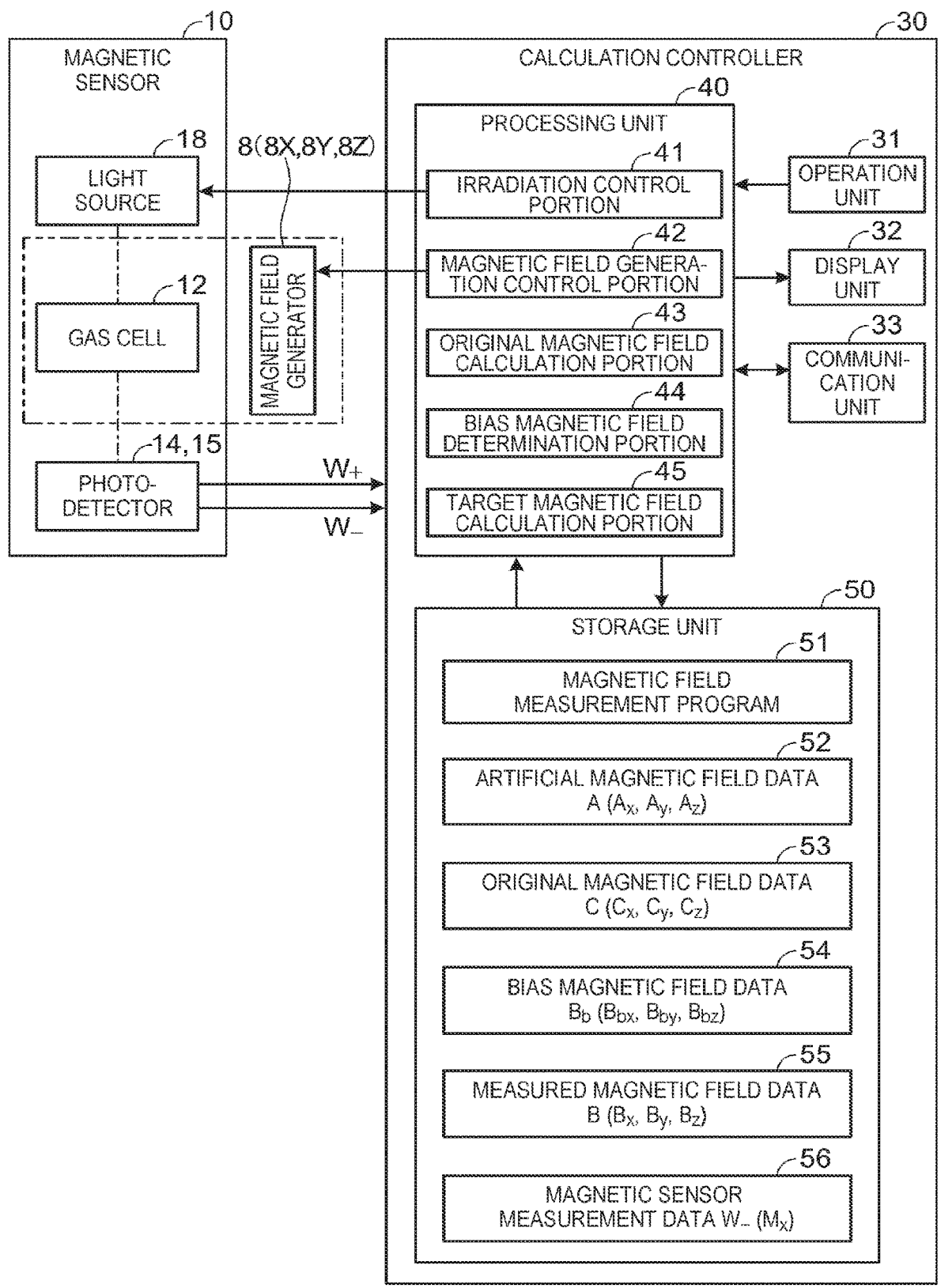
FIG. 7 is a functional configuration diagram illustrating a calculation controller according to the present embodiment.

First, a configuration example of a magnetic field measurement apparatus according to the present embodiment will be described. FIG. 1 is a schematic side view illustrating an example of a configuration of a magnetic field measurement apparatus according to the present embodiment. FIG. 2 is a schematic diagram illustrating a configuration of a magnetic field generator according to the present embodiment, and, specifically, is a diagram viewed from a Y direction. FIG. 3 is a schematic diagram illustrating the configuration of the magnetic field generator according to the present embodiment, and, specifically, is a diagram viewed from an X direction. FIG. 4 is a schematic diagram illustrating the configuration of the magnetic field generator according to the present embodiment, and, specifically, is a diagram viewed from a Z direction. FIG. 5 is a schematic diagram illustrating a configuration of a magnetic sensor according to the present embodiment, and, specifically, is a plan view viewed from the Z direction. FIG. 6 is a schematic diagram illustrating the configuration of the magnetic sensor according to the present embodiment, and, specifically, is a side view viewed from the Y direction. FIG. 7 is a functional configuration diagram illustrating a calculation controller according to the present embodiment.

A magnetic field measurement apparatus 1 illustrated in FIG. 1 is a measurement apparatus which measures a magnetic field generated by a measurement target object as a vector quantity. An apparatus which measures some information (for example, one component, magnitude, presence or absence, or the like) of the magnetic field generated by the measurement target object is referred to as a magnetism measurement apparatus. In the present embodiment, it is assumed that a measurement target object is the human body (subject), and a magnetic field generated by the measurement target object is a heart magnetic field (a magnetic field generated due to electrophysiological activity of the heart) or a brain magnetic field. Herein, as an example, a description will be made of a case where the magnetic field measurement apparatus 1 is a measurement apparatus which measures the heart magnetic field as a vector quantity.

The magnetic field measurement apparatus 1 is an apparatus which measures a magnetic field using an optical pumping method, and is a so-called one-beam type using pump light and probe light together. The magnetic field measurement apparatus 1 is not limited to the one-beam type, and may have a so-called two-beam type configuration in which a light source for applying pump light and a light source for applying probe light are separately provided. As illustrated in FIG. 1, the magnetic field measurement apparatus 1 includes a foundation 3, a table 4, a magnetic shield device 6, a magnetic field generator 8, a magnetic sensor 10, and a calculation controller 30 (refer to FIG. 7).

In the magnetic sensor 10 illustrated in FIG. 6, a direction (irradiation direction) of laser light (also referred to as irradiation light) 18a emitted from a light source 18 that passes through a gas cell 12 is assumed to be a third direction (the Z direction in the present embodiment). An oscillation direction of a linearly polarized light component of the irradiation light is assumed to be a second direction (the Y direction in the present embodiment). A direction perpendicular to the second direction (Y direction) and the third direction (Z direction) is assumed to be a first direction (the X direction in the present embodiment). The first direction (X direction), the second direction (Y direction), and the third direction (Z direction) are used as axial directions of an orthogonal coordinate system, and are hereinafter respectively referred to as an X axis direction, a Y axis direction, and a Z axis direction.

In FIG. 1, the Z axis direction is a vertical direction, and is a height direction (upward and downward directions in FIG. 1) of the magnetic field measurement apparatus 1. The X axis direction and the Y axis direction are horizontal directions, and are directions in which upper surfaces of the foundation 3 and the table 4 extend. It is assumed that a height direction (left and right directions in FIG. 1) of a subject 9 which horizontally lies is along the X axis direction. Therefore, a direction intersecting the height direction of the subject 9 (a direction which is directed out of the plane of FIG. 1) is the Y axis direction.

The foundation 3 is disposed on a bottom surface inside the magnetic shield device 6 (main body portion 6a) and extends to the outside of the main body portion 6a in the X axis direction which is a direction in which the subject 9 can be moved. The table 4 includes a first table 4a, a second table 4b, and a third table 4c. The first table 4a which is moved in the X axis direction by a linear motion mechanism 3a is provided on the foundation 3. The second table 4b which is lifted in the Z axis direction by a lifting device (not illustrated) is provided on the first table 4a. The third table 4c which is moved on a rail in the Y axis direction by a linear motion mechanism (not illustrated) is provided on the second table 4b.

The magnetic shield device 6 includes the square tubular main body portion 6a having an opening 6b. The inside of the main body portion 6a is hollow, and a sectional shape of a plane (a plane of a Y-Z section perpendicular to the X axis direction) formed by the Y axis direction and the Z axis direction is a substantially square shape. When a heart magnetic field is measured, the subject 9 is accommodated inside the main body portion 6a in a lying on the table 4. The main body portion 6a extends in the X axis direction and thus functions as a passive magnetic shield.

The foundation 3 protrudes out of the opening 6b of the main body portion 6a in the +X direction. As a size of the magnetic shield device 6, a length thereof in the X axis direction is about 200 cm, for example, and one side of the opening 6b is about 90 cm. The subject 9 laid down on the table 4 can be moved so as to come in and out of the magnetic shield device 6 from the opening 6b along with the table 4 in the X axis direction on the foundation 3.

The main body portion 6a of the magnetic shield device 6 is made of a ferromagnetic material having a relative permeability of, for example, several thousands or more, or a conductor having high conductivity. As the ferromagnetic material, permalloy, ferrite, iron, chromium, cobalt-based amorphous metal, or the like may be used. As the conductor having high conductivity, for example, aluminum which has a magnetic field reduction effect due to an eddy current effect may be used. The main body portion 6a may be formed by alternately stacking a ferromagnetic material and a conductor having high conductivity.

The magnetic field generator 8 is provided inside the main body portion 6a. The magnetic field generator 8 is constituted of three-axis Helmholtz coils, and can generate predetermined magnetic fields in each of the X axis direction, the Y axis direction, and the Z axis direction in a measurement region 5. In other words, the magnetic field generator 8 includes at least first magnetic field generators 8X which generate a magnetic field in the X axis direction, second magnetic field generators 8Y which generate a magnetic field in the Y axis direction, and preferably further includes third magnetic field generators 8Z which generate a magnetic field in the Z axis direction.

In the present embodiment, the magnetic field generator 8 includes the first magnetic field generators (a pair of Helmholtz coils which oppose each other in the X axis direction) 8X, the second magnetic field generators (a pair of Helmholtz coils which oppose each other in the Y axis direction) 8Y, and the third magnetic field generators (a pair of Helmholtz coils which oppose each other in the Z axis direction) 8Z. A measurement target region of a heart magnetic field in the magnetic field measurement apparatus 1 inside the main body portion 6a of the magnetic shield device 6 is the measurement region 5. The chest 9a of the subject 9 as a measurement position and the magnetic sensor 10 are disposed inside the measurement region 5.

As illustrated in FIGS. 2 to 4, each of diameters of the Helmholtz coils 8X, the Helmholtz coils 8Y, and the Helmholtz coils 8Z included in the magnetic field generator 8 is larger than a diameter of the measurement region 5. In other words, the measurement region 5 is included in a region surrounded by the first magnetic field generators 8X, the second magnetic field generators 8Y, and the third magnetic field generators 8Z. The centers of the Helmholtz coils 8X, 8Y and 8Z, the center of the measurement region 5, and the center of the magnetic sensor 10 preferably substantially match each other. In the above-described way, a magnetic field expressed as three-dimensional vectors can be measured with high accuracy in the measurement region 5.

A distance between the pair of opposing Helmholtz coils is preferably more than a diameter of each of the other Helmholtz coils. For example, as illustrated in FIGS. 2 to 4, a distance between the pair of opposing Helmholtz coils 8X is preferably more than a diameter of each of the Helmholtz coils 8Y and the Helmholtz coils 8Z. In the above-described way, it is possible to generate uniform magnetic fields parallel to the Y axis (or the Z axis) with the pair of Helmholtz coils 8Y (or 8Z). Similarly, a distance between the pair of opposing Helmholtz coils 8Y (or 8Z) is preferably more than a diameter of each of the other Helmholtz coils.

In FIGS. 2 to 4, it is assumed that the distance (for example, in FIG. 2, the distance between the left Helmholtz coil 8X and the right Helmholtz coil 8X along the X axis) between the pair of opposing Helmholtz coils 8X is less than the diameter of each of the Helmholtz coils 8Y and the Helmholtz coils 8Z. In this case, the Helmholtz coils 8X enter a columnar-shape region which has the pair of Helmholtz coils 8Y (or 8Z) as bottoms. Then, magnetic fields formed by the pair of Helmholtz coils 8Y (or 8Z) are distorted, and thus it is unlikely to generate uniform magnetic fields which are parallel to the Y axis (or the Z axis) in the vicinity of the measurement region 5.

In contrast, in a case where the distance between the pair of opposing Helmholtz coils 8X is more than the diameter of each of the Helmholtz coils 8Y and the Helmholtz coils 8Z, the Helmholtz coils 8X are disposed outside the circumferential region which has the Helmholtz coils 8Y (or 8Z) as bottoms. Therefore, distortion of magnetic fields formed by the pair of Helmholtz coils 8Y (or 8Z) is minimized by the Helmholtz coils 8X, and thus it is possible to generate uniform magnetic fields which are parallel to the Y axis (or the Z axis) in the vicinity of the measurement region 5.

As mentioned above, the pair of Helmholtz coils 8Y and the pair of Helmholtz coils 8Z are preferably disposed outside the circumferential region which has the pair of Helmholtz coils 8X as the bottoms. In addition, the pair of Helmholtz coils 8Z and the pair of Helmholtz coils 8X are preferably disposed outside the circumferential region which has the pair of Helmholtz coils 8Y as the bottoms, and the pair of Helmholtz coils 8X and the pair of Helmholtz coils 8Y are preferably disposed outside the circumferential region which has the pair of Helmholtz coils 8Z as the bottoms.

In the present embodiment, a shape of the Helmholtz coil is described as a circular shape, but a shape of the Helmholtz coil is not limited to the circular shape and may be a polygonal shape such as a square shape. In a case where a shape of the Helmholtz coil is a polygonal shape, remaining Helmholtz coils perpendicular to a height direction of a prism are disposed outside a prismatic region which has a pair of Helmholtz coils as bottoms.

The magnetic sensor 10 is fixed to a ceiling of the main body portion 6a via a supporting member 7. The magnetic sensor 10 measures an intensity component of a magnetic field in the Z axis direction of the measurement region 5. The magnetic sensor 10 measures a magnetic field using an optical pumping method. When a heart magnetic field of the subject 9 is measured, the first table 4a and the third table 4c are moved so that the chest 9a of the subject 9 which is a measurement position is located so as to face the magnetic sensor 10, and the second table 4b is lifted so that the chest 9a becomes close to the magnetic sensor 10.

In measurement of a weak magnetic field using the optical pumping type magnetic sensor 10, it is preferable to cancel out a magnetic field (original magnetic field) which comes from the outside due to environments such as the Earth's magnetic field or urban noise which is present in the measurement region 5 in which the gas cell 12 is disposed. This is because, if the original magnetic fields are present, sensitivity for a magnetic field generated by a measurement target object (subject 9) is reduced, or measurement accuracy is reduced, due to an influence thereof. In the present embodiment, the magnetic shield device 6 prevents a magnetic field from entering the measurement region 5 from the outside. The magnetic field generator 8 disposed inside the main body portion 6a can maintain the vicinity of the measurement region 5 in a low magnetic field state close to zero.

As illustrated in FIG. 5, the magnetic sensor 10 includes the light source 18, the gas cell 12, and photodetectors 14 and 15. The light source 18 outputs the laser light 18a with a wavelength corresponding to an absorption line of cesium. A wavelength of the laser light 18a is not particularly limited, but is set to a wavelength of 894 nm corresponding to the D1-line, in the present embodiment. The light source 18 is a tunable laser device, and the laser light 18a output from the light source 18 is continuous light with a predetermined light amount.

In the present embodiment, the light source 18 is provided in the calculation controller 30. The laser light 18a emitted from the light source 18 is supplied to a main body of the magnetic sensor 10 via an optical fiber 19. The main body of the magnetic sensor 10 and the optical fiber 19 are connected to each other via an optical connector 20. The laser light 18a supplied via the optical connector 20 travels in the −Y direction and is incident to a polarization plate 21. The laser light 18a having passed through the polarization plate 21 is linearly polarized. The laser light 18a is sequentially incident to a first half mirror 22, a second half mirror 23, a third half mirror 24, and a first reflection mirror 25.

Some of the laser light 18a is reflected by the first half mirror 22, the second half mirror 23, and the third half mirror 24 so as to travel in the +X direction, and the other light 18a is transmitted therethrough so as to travel in the −Y direction. The first reflection mirror 25 reflects the entire incident laser light 18a in the +X direction. An optical path of the laser light 18a is divided into four optical paths by the first half mirror 22, the second half mirror 23, the third half mirror 24, and the first reflection mirror 25. Reflectance of each mirror is set so that light intensities of the laser light 18a on the respective optical paths are the same as each other.

Next, as illustrated in FIG. 6, the laser light 18a is sequentially applied and incident to a fourth half mirror 26, a fifth half mirror 27, a sixth half mirror 28, and a second reflection mirror 29. Some of the laser light 18a is reflected by the fourth half mirror 26, the fifth half mirror 27, and the sixth half mirror 28 so as to travel in the +Z direction, and the other laser light 18a is transmitted therethrough so as to travel in the +X direction. The second reflection mirror 29 reflects the entire incident laser light 18a in the +Z direction.

A single optical path of the laser light 18a is divided into four optical paths by the fourth half mirror 26, the fifth half mirror 27, the sixth half mirror 28, and the second reflection mirror 29. Reflectance of each mirror is set so that light intensities of the laser light 18a on the respective optical paths are the same as each other. Therefore, the optical path of the laser light 18a is divided into the sixteen optical paths. In addition, reflectance of each mirror is set so that light intensities of the laser light 18a on the respective optical paths are the same as each other.

The sixteen gas cells 12 of four rows and four columns are provided on the respective optical paths of the laser light 18a on the +Z direction side of the fourth half mirror 26, the fifth half mirror 27, the sixth half mirror 28, and the second reflection mirror 29. The laser light 18a reflected by the fourth half mirror 26, the fifth half mirror 27, the sixth half mirror 28, and the second reflection mirror 29 pass through the gas cells 12.

The gas cell 12 is a box having a cavity therein, and an alkali metal gas is enclosed in the cavity as a medium for changing optical characteristics of light according to a magnetic field in the measurement region 5 (refer to FIG. 1). The alkali metal is not particularly limited, and potassium, rubidium, or cesium may be used. In the present embodiment, for example, cesium is used as the alkali metal.

A polarization separator 13 is provided on the +Z direction side of each gas cell 12. The polarization separator 13 is an element which separates the incident laser light 18a into two polarization components of the laser light 18a, which are perpendicular to each other. As the polarization separator 13, for example, a Wollaston prism or a polarized beam splitter may be used.

The photodetector 14 is provided on the +Z direction side of the polarization separator 13, and the photodetector 15 is provided on the +X direction side of the polarization separator 13. The laser light 18a having passed through the polarization separator 13 is incident to the photodetector 14, and the laser light 18a reflected by the polarization separator 13 is incident to the photodetector 15. The photodetector 14 and the photodetector 15 output signals corresponding to an amount of incident laser light 18a which is received, to the calculation controller 30.

If the photodetectors 14 and 15 generate magnetic fields, this may influence measurement, and thus the photodetectors 14 and 15 may be made of a non-magnetic material. The magnetic sensor 10 includes heaters 16 which are provided on both sides in the X axis direction and both sides in the Y axis direction. Each of the heaters 16 preferably has a structure in which a magnetic field is not generated, and may employ, for example, a heater of a type of performing heating by causing steam or hot air to pass through a flow passage. Instead of using a heater, the gas cell 12 may be inductively heated using a high frequency voltage.

The magnetic sensor 10 is disposed on the +Z direction side of the subject 9 (refer to FIG. 1). A magnetic field vector B (including a target magnetic field vector generated by a measurement target object) which is detected in the measurement region 5 by the magnetic sensor 10 enters the magnetic sensor 10 from the −Z direction side. The magnetic field vector B passes through the fourth half mirror 26 to the second reflection mirror 29, passes through the gas cell 12, then passes through the polarization separator 13, and comes out of the magnetic sensor 10.

The magnetic sensor 10 is a sensor which is called an optical pumping type magnetic sensor or an optical pumping atom magnetic sensor. Cesium in the gas cell 12 is heated and is brought into a gaseous state. The cesium gas is irradiated with the linearly polarized laser light 18a, and thus cesium atoms are excited, and thus orientations of magnetic moments can be aligned. When the magnetic field vector B passes through the gas cell 12 in this state, the magnetic moments of the cesium atoms precess due to a magnetic field of the magnetic field vector B. This precession is referred to as Larmore precession.

The magnitude of the Larmore precession has a positive correlation with the strength of the magnetic field vector B. In the Larmore precession, a polarization plane of the laser light 18a is rotated. The magnitude of the Larmore precession has a positive correlation with a change amount of a rotation angle of the polarization plane of the laser light 18a. Therefore, the strength of the magnetic field vector B has a positive correlation with the change amount of a rotation angle of the polarization plane of the laser light 18a. The sensitivity of the magnetic sensor 10 is high in the Z axis direction in the magnetic field vector B, and is low in the direction perpendicular to the Z axis direction.

The polarization separator 13 separates the laser light 18a having passed through the gas cell 12 into two components of linearly polarized light in axial directions (an α axis and a β axis illustrated in FIG. 11) which are perpendicular to each other. One separated linearly polarized light is guided to the photodetector 14, and the other linearly polarized light is guided to the photodetector 15. The photodetector 14 and the photodetector 15 respectively receive the two components of linearly polarized light perpendicular to each other, generate signals corresponding to amounts of the received light, and output the signals to the calculation controller 30. The strength of each of the linearly polarized light beams is detected, and thus a rotation angle of a polarization plane of the laser light 18a can be detected. The strength of the magnetic field vector B can be detected on the basis of a change of the rotation angle of the polarization plane of the laser light 18a.

An element constituted of the gas cell 12, the polarization separator 13, the photodetector 14, and the photodetector 15 is referred to as a sensor element 11. In the present embodiment, sixteen sensor elements 11 of four rows and four columns are disposed in the magnetic sensor 10. The number and arrangement of the sensor elements 11 in the magnetic sensor 10 are not particularly limited. The sensor elements 11 may be disposed in three or less rows or five or more rows. Similarly, the sensor elements 11 may be disposed in three or less columns or five or more columns. The larger the number of sensor elements 11, the higher the spatial resolution.

As illustrated in FIG. 7, the calculation controller 30 includes an operation unit 31, a display unit 32, a communication unit 33, a processing unit 40, and a storage unit 50. The operation unit 31 is an input device such as a button switch, a touch panel, a keyboard, or various sensors, and outputs an operation signal corresponding to a performed operation to the processing unit 40. Various input instructions such as an instruction for starting magnetic field measurement are performed using the operation unit 31.

The display unit 32 is a display device such as a liquid crystal display (LCD), and performs various display based on a display signal from the processing unit 40. A measurement result or the like is displayed on the display unit 32. The communication unit 33 is a communication device such as a wireless communication device, a modem, a wired communication cable jack, or a control circuit, and is connected to a predetermined communication line so as to perform communication with external devices.

The processing unit 40 is constituted of a microprocessor such as a central processing unit (CPU) or a graphics processing unit (GPU), or an electronic component such as an application specific integrated circuit (ASIC) or an integrated circuit (IC) memory. The processing unit 40 performs various calculation processes on the basis of a predetermined program or data, an operation signal from the operation unit 31, a measurement signal from the magnetic sensor 10, and the like, so as to control an operation of the calculation controller 30.

The processing unit 40 includes an irradiation control portion 41, a magnetic field generation control portion 42, an original magnetic field calculation portion 43, a bias magnetic field determination portion 44, and a target magnetic field calculation portion 45. The processing unit 40 performs a magnetism measurement process (refer to a flowchart shown in FIG. 13) according to a magnetic field measurement program 51 stored in the storage unit 50.

In the magnetism measurement process according to the present embodiment, prior to measurement of a magnetic field generated by a measurement target object such as the heart or the brain of the human body, an original magnetic field $C_x$ of the measurement region 5 is calculated as an initial setting in a state in which the measurement target object is not placed. A magnetic field generated by the measurement target object is measured in a state in which a bias magnetic field which cancels out the original magnetic field $C_x$ is generated by the magnetic field generator 8. In other words, measurement of the magnetic field generated by the measurement target object (subject 9) is performed in a state in which an external magnetic field (original magnetic field) coming into the measurement region 5 is reduced.

The irradiation control portion 41 controls the light source 18 of the magnetic sensor 10 to perform irradiation with irradiation light. Specifically, the irradiation control portion 41 controls not only starting or ending of irradiation with irradiation light in the light source 18 but also intensity of the irradiation light, a direction of a linear polarization plane included in the irradiation light, and the like.

The magnetic field generation control portion 42 controls the magnetic field generator 8 (8X, 8Y, and 8Z) to generate predetermined magnetic fields in the X, Y and Z axis directions, respectively. Specifically, the magnetic field generation control portion 42 causes the magnetic field generator 8 (8X, 8Y, and 8Z) to generate a predetermined artificial magnetic field A ($A_x$, $A_y$, $A_z$) at the initial setting. As will be described later in detail, the artificial magnetic field A is an alternating magnetic field f ($\omega$t) in which a first direction (X direction) component and a second direction (Y direction) component thereof have the same amplitude and cycle and different phases, and is a magnetic field vector in which a third direction (Z direction) component thereof is zero ($A_z$=0). The artificial magnetic field A ($A_x$, $A_y$, $A_z$) is stored as artificial magnetic field data 52 in the storage unit 50.

During measurement, the magnetic field generation control portion 42 causes the magnetic field generator 8 (8X, 8Y, and 8Z) to generate a combined magnetic field ($B_b$+A) of a bias magnetic field $B_b$ ($B_{bx}$, $B_{by}$, $B_{bz}$) determined by the bias magnetic field determination portion 44 and the artificial magnetic field A ($A_x$, $A_y$, $A_z$).

The magnetic field generators 8X may sequentially generate a constant magnetic field with an X side first level, a constant magnetic field with an X side second level, and a constant magnetic field with an X side third level, as the X axis direction component $A_x$ of the artificial magnetic field A. Similarly, the magnetic field generators 8Y may sequentially generate a constant magnetic field with an Y side first level, a constant magnetic field with an Y side second level, and a constant magnetic field with an Y side third level, as the Y axis direction component $A_y$ of the artificial magnetic field A. In addition, the magnetic field generators 8X may sequentially generate a constant magnetic field with an X side first level and a constant magnetic field with an X side second level, as the X axis direction component $A_x$ of the artificial magnetic field A, and the magnetic field generators 8Y may sequentially generate a constant magnetic field with an Y side first level and a constant magnetic field with an Y side second level as the Y axis direction component $A_y$ of the artificial magnetic field A.

The original magnetic field calculation portion 43 calculates an original magnetic field vector C ($C_x$, $C_y$, $C_z$) on the basis of a signal output from the magnetic sensor 10 in a state in which the magnetic field generator 8 (8X, 8Y, and 8Z) generates the artificial magnetic field vector A ($A_x$, $A_y$, $A_z$). Specifically, a magnetic sensor measurement value (square difference $W_-$) obtained on the basis of the signal output from the magnetic sensor 10 is set as a spin polarization degree $M_x$, and three or more combinations of a value $A_x(t)$ of the X axis direction component $A_x$ of the artificial magnetic field vector A, a value $A_y(t)$ of the Y axis direction component $A_y$ thereof, and a spin polarization degree $M_x(t)$ at a certain time point t and having different spin polarization degrees $M_x$ are acquired.

In addition, simultaneous equations formed of three or more equations which are obtained by assigning each of the acquired combinations to Equation 17 to be described later are defined, and the original magnetic field vector C ($C_x$, $C_y$, $C_z$) is calculated by performing a predetermined arithmetic calculation process for solving the simultaneous equations. The calculated original magnetic field C ($C_x$, $C_y$, $C_z$) is stored as original magnetic field data 53 in the storage unit 50.

The bias magnetic field determination portion 44 determines the bias magnetic field $B_b$ ($B_{bx}$, $B_{by}$, $B_{bz}$) which cancels out the original magnetic field vector C ($C_x$, $C_y$, $C_z$) calculated by the original magnetic field calculation portion 43. The determined bias magnetic field $B_b$ ($B_{bx}$, $B_{by}$, $B_{bz}$) is stored as bias magnetic field data 54 in the storage unit 50.

The target magnetic field calculation portion 45 calculates a target magnetic field vector B ($B_x$, $B_y$, $B_z$) generated by a measurement target object on the basis of a signal output from the magnetic sensor 10 in a state in which the measurement target object is disposed and the magnetic field generator 8 generates the bias magnetic field $B_b$. Specifically, a measurement value (square difference $W_-$) obtained on the basis of the signal output from the magnetic sensor 10 is set as a spin polarization degree $M_x$, and three or more combinations of a value $A_x(t)$ of the X axis direction component $A_x$ of the artificial magnetic field vector A, a value $A_y(t)$ of the Y axis direction component $A_y$ thereof, and a spin polarization degree $M_x(t)$ at a certain time point t and having different spin polarization degrees $M_x$ are acquired.

In addition, simultaneous equations formed of three or more equations which are obtained by assigning each of the acquired combinations to Equation 17 to be described later are defined, and the original magnetic field vector C ($C_x$, $C_y$, $C_z$) is calculated as the target magnetic field B ($B_x$, $B_y$, $B_z$) generated by the measurement target object by performing a predetermined arithmetic calculation process for solving the simultaneous equations. The calculated target magnetic field vector B ($B_x$, $B_y$, $B_z$) is stored as measured magnetic field data 55 in the storage unit 50. The magnetic sensor measurement value (square difference $W_-$) obtained on the basis of a signal output from the magnetic sensor 10 is stored as magnetic sensor measurement data 56 in the storage unit 50.

The storage unit 50 is constituted of a storage device such as a read only memory (ROM), a random access memory (RAM), or a hard disk. The storage unit 50 stores a program, data, or the like for the processing unit 40 integrally controlling the calculation controller 30, and is used as a work area of the processing unit 40 so as to temporarily store results of calculation performed by the processing unit 40, operation data from the operation unit 31, or the like. In the present embodiment, the storage unit 50 stores a magnetic field measurement program 51, the artificial magnetic field data 52, the original magnetic field data 53, the bias magnetic field data 54, the measured magnetic field data 55, and the magnetic sensor measurement data 56.

Principle

Figure 8:
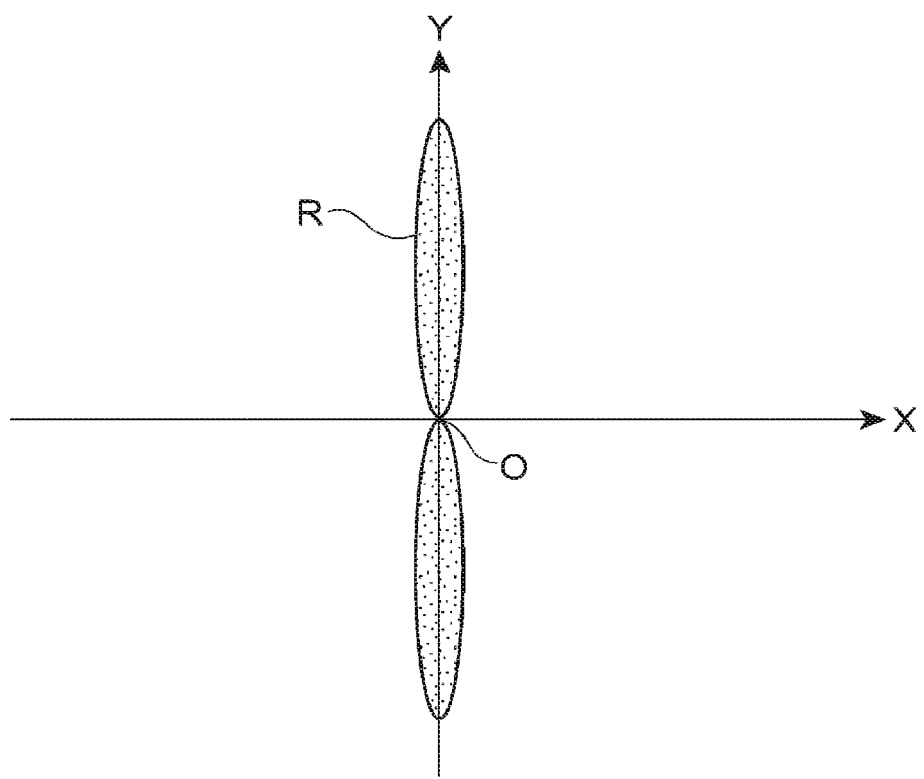
FIG. 8 is a diagram for explaining an alignment in a case where there is no magnetic field.
Figure 9:
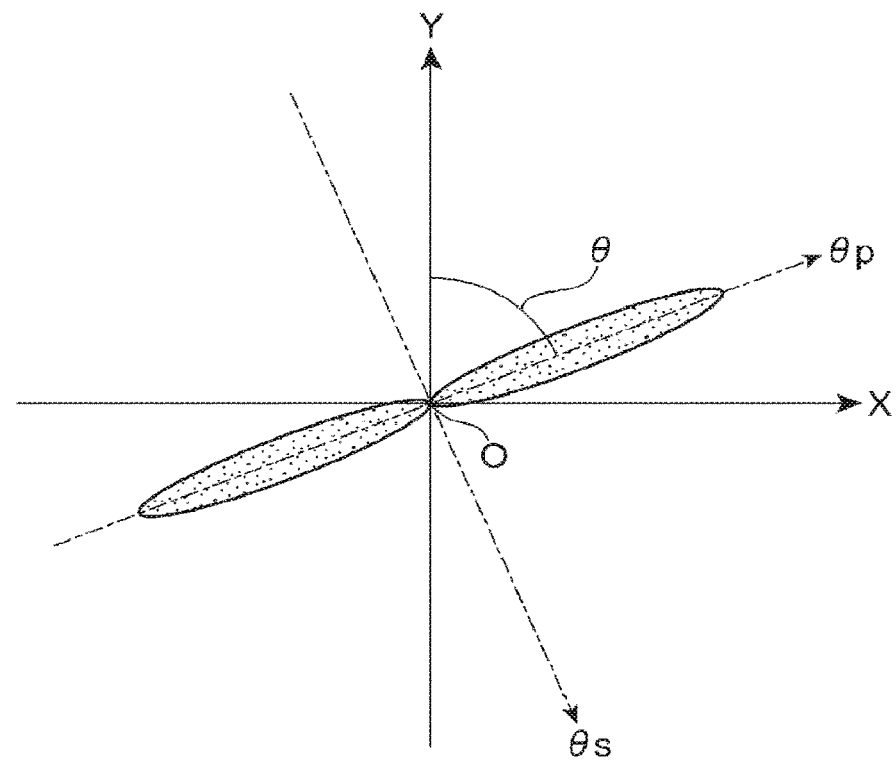
FIG. 9 is a diagram for explaining a change in the alignment due to a magnetic field.
Figure 10:
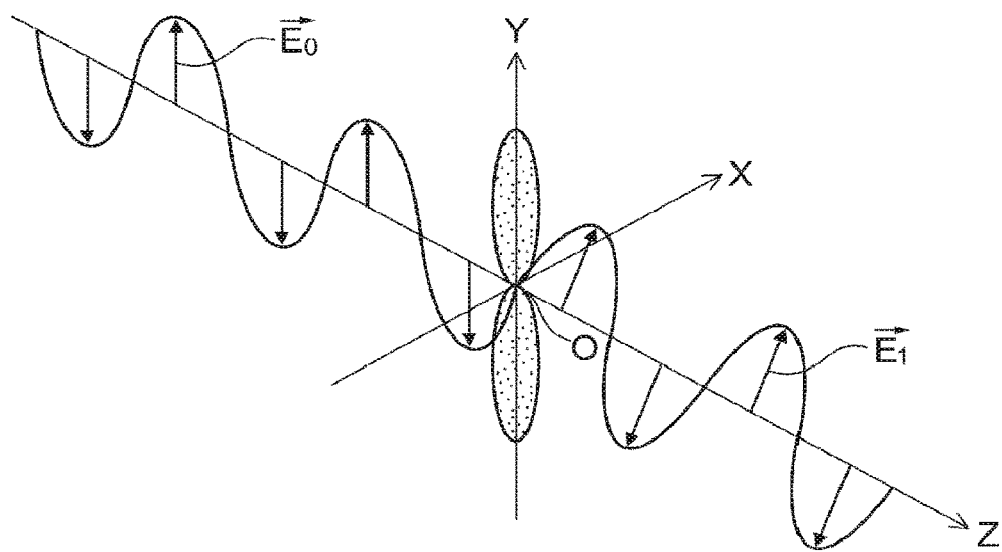
FIG. 10 is a diagram for explaining a change in a polarization plane of linearly polarized light due to transmission into a gas cell.
Figure 11:
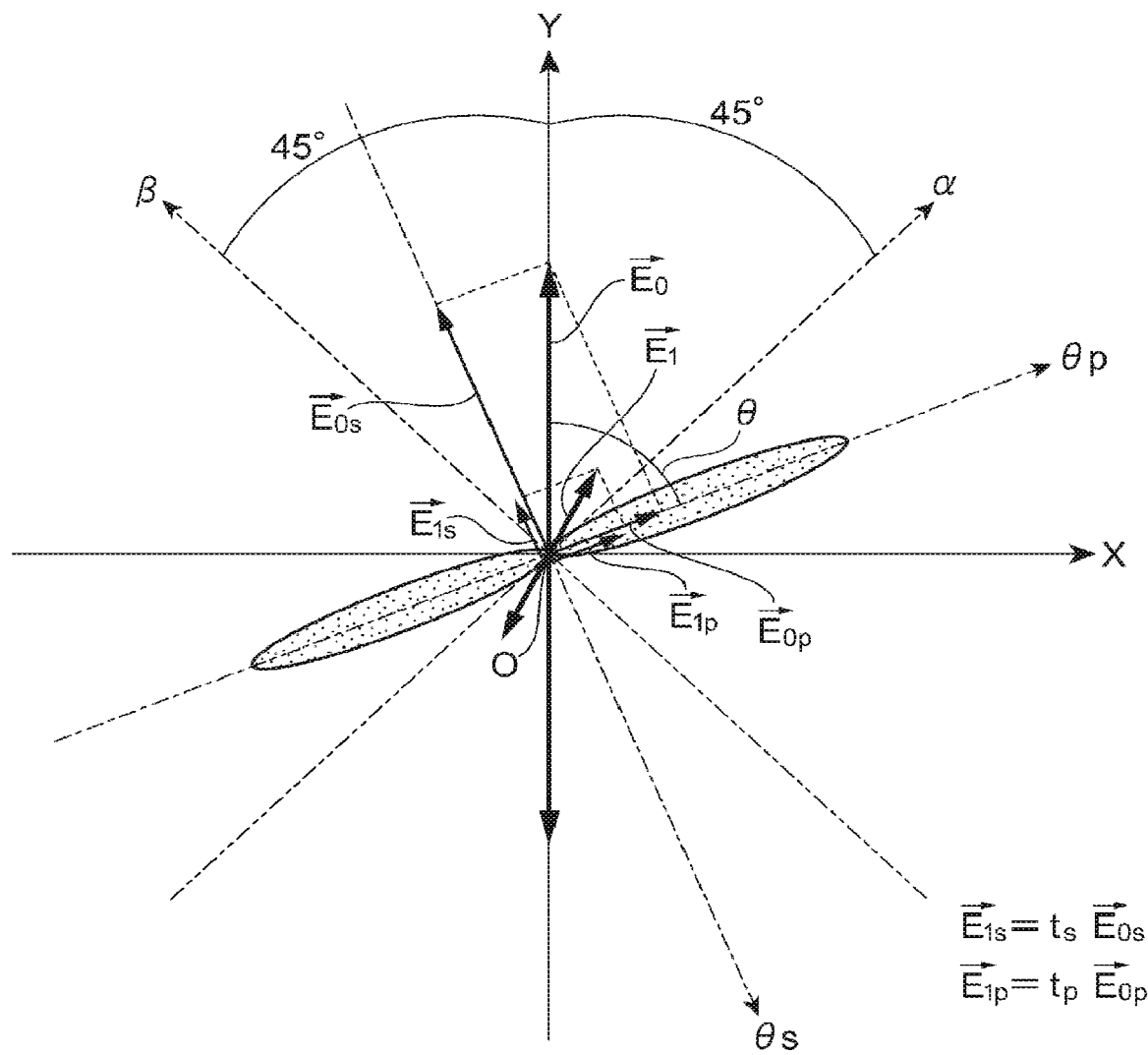
FIG. 11 is a diagram for explaining a change in a polarization plane of linearly polarized light due to transmission into a gas cell.
Figure 12:
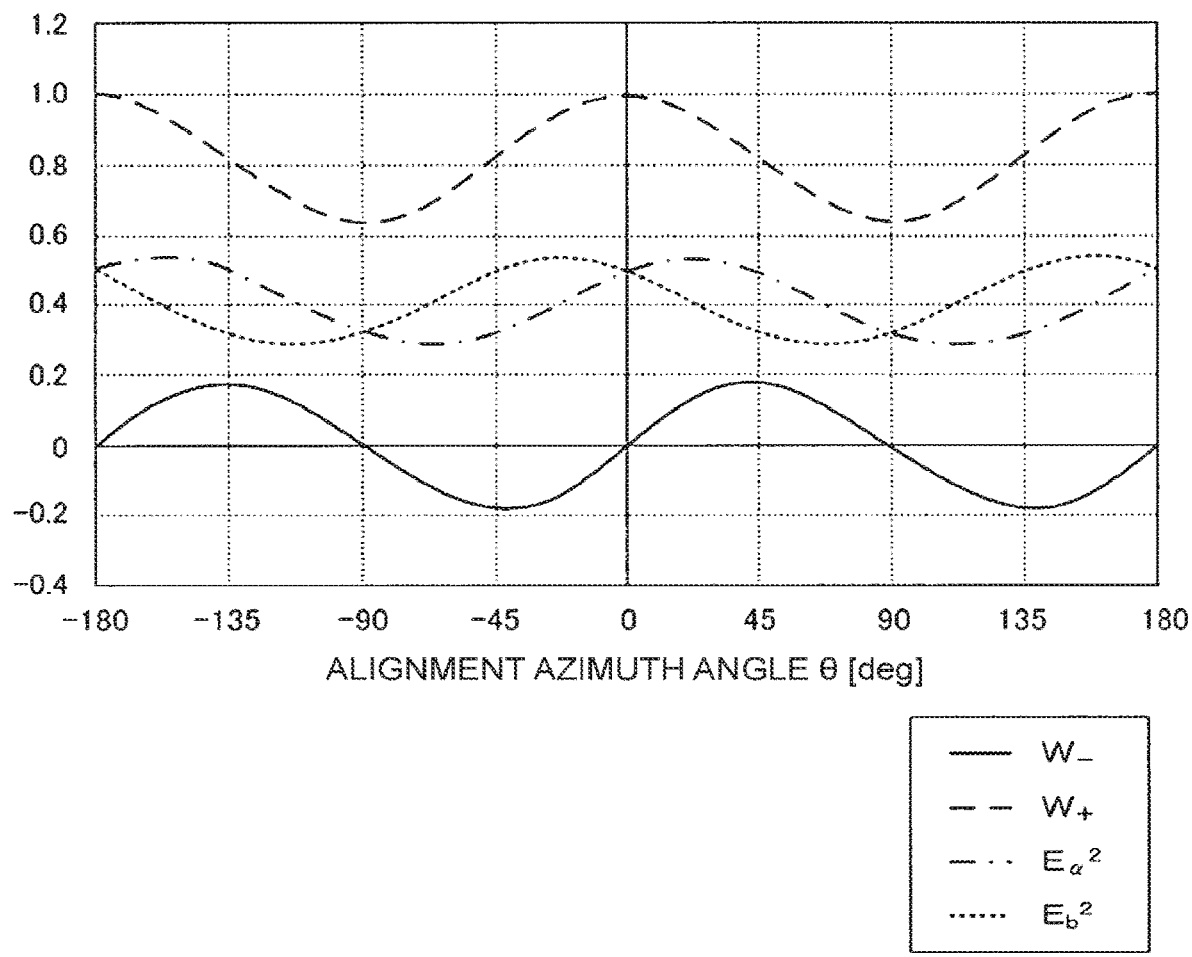
FIG. 12 is a diagram illustrating a relationship between an alignment azimuth angle θ and a detection result of probe light.

A description will be made of a magnetic field measurement principle in the magnetic field measurement apparatus 1. FIG. 8 is a diagram for explaining an alignment in a case where there is no magnetic field. FIG. 9 is a diagram for explaining a change in the alignment due to a magnetic field. FIGS. 10 and 11 are diagrams for explaining a change in a polarization plane of linearly polarized light due to transmission into the gas cell. FIG. 12 is a diagram illustrating a relationship between an alignment azimuth angle $\theta$ and a detection result of probe light.

In the following description, for better understanding of the principle, the description is made in a time series, but, actually, (A) optical pumping and (C) probing may simultaneously occur in a one-beam method of the present embodiment.

(A) Optical Pumping

The gaseous alkali metal atoms enclosed in the gas cell 12 are irradiated with pump light (light passing through the gas cell 12 in the present embodiment) which is adjusted to a wavelength corresponding to a transition from a state of the hyperfine structure quantum number F to a state of F' (=F−1) in the D1-line, and are thus brought into a group in which (spin-polarized) atoms whose spins are directed in anti-parallel directions (opposite directions) exist in substantially the same number. This state is referred to as an alignment. The spin polarization of a single atom is alleviated with the passage of time, but since the pump light is continuous wave (CW) light, formation and alleviation of spin polarization are repeatedly performed simultaneously and continuously, and, as a result, steady spin polarization is formed in terms of the entire atom group.

In a case where the measurement region 5 is a zero magnetic field, the alignment is expressed by a probability distribution of magnetic moments of the atoms. In a case where the pump light is linearly polarized light as in the present embodiment, as illustrated in FIG. 8, a shape thereof is a shape of a region R in which two ellipses growing in oscillation directions (the Y axis direction in the present embodiment) of an electric field of the linearly polarized light of the pump light are connected to each other on the X-Y plane.

(B) Action of Magnetic Field

If a certain magnetic field is present in the measurement region 5, the alkali metal atom starts to precess with a direction of a magnetic field vector (a magnetic field received by the gas cell 12) as a rotation axis. As illustrated in FIG. 9, the direction (a direction along a major axis of the ellipse) of the alignment changes so as to be rotated with the origin O as a center, due to an addition of an optical pumping action caused by the pump light and an alleviation action caused by a collision of the gaseous atom into the inner wall of the gas cell 12.

The direction of the alignment is brought into a steady state in an arrangement of being rotated about the Y axis by an angle ($\theta$) corresponding to the strength of the magnetic field. Here, an alignment direction is indicated by $\theta p$, and a direction perpendicular thereto is indicated by $\theta s$. An angle $\theta$ formed between the Y axis direction which is the oscillation direction of the electric field of the pump light and the alignment direction $\theta p$ is referred to as an alignment azimuth angle $\theta$. The alignment azimuth angle $\theta$ mainly increases according to the magnetic field strength in the Z axis direction.

(C) Probing

It is assumed that probe light (light passing through the gas cell 12 in the present embodiment) having a linearly polarized light component of which an electric field vector $E_0$ oscillates in the Y axis direction passes through the atom group in this state. In other words, as illustrated in FIG. 10, the linearly polarized light in which an oscillation direction of an electric field of the probe light is the Y axis direction is caused to pass through the gas cell 12 in the +Z direction. In FIG. 10, the origin O corresponds to a position of the atom group (the gaseous atoms enclosed in the gas cell 12), and the atom group is optically pumped so that the alignment occurs which is distributed in the region along the Y axis direction. In the Z axis direction, the −Z direction side shows linearly polarized light before being transmitted through the atom group, and the +Z direction shows linearly polarized light (transmitted light) after being transmitted through the atom group.

If the linearly polarized light is transmitted through the atom group, a polarization plane of the linearly polarized light is rotated due to linear dichroism, and the electric field vector changes to $E_1$. The linear dichroism is a property in which transmittance of the linearly polarized light differs in the direction $\theta p$ (refer to FIG. 9) of the alignment and in the direction $\theta s$ (refer to FIG. 9) perpendicular to the alignment. Specifically, since a component in the direction $\theta s$ perpendicular to the alignment is absorbed more than a component in the direction $\theta p$ of the alignment, the polarization plane of the probe light is rotated so as to become close to the direction $\theta p$ of the alignment.

FIG. 11 is a diagram illustrating a state of rotation of the polarization plane before and after the linearly polarized light is transmitted through the atom group on the X-Y plane perpendicular to the Z axis direction which is an irradiation direction of the probe light. In the present embodiment, the probe light incident to the gas cell 12 is linearly polarized light of the electric field vector $E_0$ in which an oscillation direction of the electric field is the Y axis direction. Due to the alignment, the component in the direction $\theta p$ of the probe light is transmitted with the transmittance $t_p$, and the component in the direction $\theta s$ is transmitted with the transmittance $t_s$. Since $t_p > t_s$ due to the linear dichroism, the polarization plane of the probe light which has been transmitted through the gas cell 12 is rotated so as to become close to the direction $\theta p$. In this way, the light having passed through the gas cell 12 has the electric field vector $E_1$.

Specifically, a component of the electric field vector $E_0$ along the alignment is indicated by $E_{0P}$, and a component of the electric field vector $E_0$ perpendicular to the alignment and a traveling direction of linearly polarized light is indicated by $E_{0S}$. A component of the electric field vector $E_1$ along the alignment is indicated by $E_{1P}$, and a component of the electric field vector $E_1$ perpendicular to the alignment and a traveling direction of linearly polarized light is indicated by $E_{1S}$. In this case, the following relationship is satisfied: $E_{1P} = t_p E_{0P}$, and $E_{1S} = t_s E_{0S}$.

If an angle (hereinafter, referred to as an "alignment azimuth angle") formed between the direction of the alignment and the oscillation direction of the electric field of the probe light is indicated by $\theta$, the respective components of the electric field vector $E_1$ in the direction $\theta p$ and the direction $\theta s$ are calculated using the following Equation 4 on the basis of the above-described relationship.

$$\vec{E}_1 = (0 \ E_0) \begin{pmatrix} \cos\theta & \sin\theta \\ -\sin\theta & \cos\theta \end{pmatrix} \begin{pmatrix} t_s & 0 \\ 0 & t_p \end{pmatrix} \quad (4)$$

As described above, the probe light which has been transmitted through the gas cell 12 is separated into two polarized light components along an $\alpha$ axis which forms +45 degrees with the Y axis direction which is an irradiation direction of the probe light and a $\beta$ axis which forms −45 degrees with the Y axis direction by the polarization separator 13. An $\alpha$ axis direction component $E_\alpha$ and a $\beta$ axis direction component $E_\beta$ of the linearly polarized light with the electric field vector $E_1$ which has been transmitted through the gas cell 12 are calculated according to Equation 5.

$$(E_\alpha \ E_\beta) = \vec{E}_1 \begin{pmatrix} \cos(-\frac{\pi}{4} - \theta) & \sin(-\frac{\pi}{4} - \theta) \\ -\sin(-\frac{\pi}{4} - \theta) & \cos(-\frac{\pi}{4} - \theta) \end{pmatrix} \quad (5)$$

The photodetectors 14 and 15 measure light intensities of the two polarized light components along the $\alpha$ axis and the $\beta$ axis, and output signals corresponding to amounts of received light to the calculation controller 30. The calculation controller 30 processes the signals from the photodetectors 14 and 15, and calculates a square sum $W_+$ and a square difference $W_-$ of the components in the directions along the $\alpha$ axis and the $\beta$ axis according to Equations 6 and 7. $E_\alpha$ indicates the light intensity of the component in the α axis direction, and $E_\beta$ indicates the light intensity of the component in the β axis direction.

$$W_+ = E_\alpha^2 + E_\beta^2 \qquad (6)$$

$$W_- = E_\alpha^2 - E_\beta^2 \qquad (7)$$

FIG. 12 illustrates the α axis direction and β axis direction components $E_\alpha$ and $E_\beta$ of the linearly polarized light with the electric field vector $E_1$, square values $E_\alpha^2$ and $E_\beta^2$ thereof, and a square sum $W_+$ and a square difference $W_-$ of the components in the directions along the α axis and the β axis, relative to the alignment azimuth angle θ. A case where the alignment azimuth angle θ is 0 indicates that the measurement region 5 is in a zero magnetic field state (refer to FIG. 8). Here, the transmittance $t_p$ of the component in the direction θp is 1, and the transmittance $t_s$ of the component in the direction θs is 0.8.

In FIG. 12, looking at the value of the square difference $W_-$, the square difference $W_-$ oscillates in a cycle of 180 degrees with respect to the alignment azimuth angle θ. The square difference $W_-$ substantially linearly changes with respect to the alignment azimuth angle θ in the range of the alignment azimuth angle θ from −45 degrees to +45 degrees, and thus high sensitivity can be obtained. Since the center of the linear change is 0 degrees, and a range of the linear change is wider than other ranges (the square sum $W_+$ and the like), this is suitable for measuring a magnetic field generated in the measurement region 5. Since a biomagnetic field such as a heart magnetic field or a brain magnetic field is weak, and the alignment azimuth angle θ is small, it is possible to observe a rotation angle of the polarization plane with high sensitivity using the square difference $W_-$.

However, as described above, if an unnecessary magnetic field which is different from a magnetic field of a measurement target object is present in the measurement region 5, sensitivity is reduced due to an influence thereof, and thus measurement accuracy is reduced. Typically, when a magnetic field of a measurement target object, such as a heart magnetic field or a brain magnetic field is measured, the measurement is performed in an environment in which the magnetic shield device 6 prevents an external magnetic field from entering the measurement region 5 (a state in which the external magnetic field is not considerable), but it is hard to sufficiently reduce the external magnetic field to an extent of not influencing the measurement depending on the magnetic shield device 6. In other words, in most cases, the magnetic shield device 6 cannot completely prevent the entry of the external magnetic field. A magnetic shield device which can completely shield a magnetic field is large-sized and expensive, and installation costs or operation costs thereof are high.

Therefore, in the present embodiment, the magnetic shield device 6 is used, an external magnetic field (referred to as an original magnetic field C) which enters the magnetic shield device 6 is measured, and a magnetic field of a measurement target object is measured in a state in which the external magnetic field is reduced using the magnetic field generator 8. However, in a case where the external magnetic field is originally low, or the external magnetic field is stable, the present embodiment can be implemented without using even the magnetic shield device 6.

According to FIG. 12, in the range of the alignment azimuth angle θ from −45 degrees to +45 degrees, the square difference $W_-$ is substantially proportional to an X axis direction component $M_x$ (hereinafter, referred to as a spin polarization degree $M_x$) of a spin polarization degree ($M_x$, $M_y$, $M_z$). The spin polarization degree $M_x$ corresponds to a magnetization value which is an X axis direction component of a magnetization vector obtained by combining magnetic moments of atoms. For this reason, hereinafter, the square difference $W_-$ is treated as the spin polarization degree $M_x$. In the present embodiment, the spin polarization degree $M_x$ is focused, and there is derivation of a relational expression indicating how a value of the spin polarization degree $M_x$ changes according to respective components $B_x$, $B_y$, and $B_z$ of the magnetic field vector B applied to the gas cell 12.

The time development of the spin polarization degree ($M_x$, $M_y$, $M_z$) of an alignment caused by optical pumping is approximated according to Bloch equations shown in the following Equations 8 to 10. $\gamma_F$ indicates a magnetic rotation ratio which is defined depending on the kind of medium gas (alkali metal atom gas) in the gas cell 12. $\Gamma_0$ indicates alleviation speed of the spin polarization degree ($M_x$, $M_y$, $M_z$), and $\Gamma_p$ indicates optical pumping speed. $M_p$ indicates the maximum magnetization when spins of the alkali metal atom group are all aligned in one direction.

$$\frac{dM_x}{dt} = \gamma_F(M_y B_z - M_z B_y) - \Gamma_0 M_x - \Gamma_p M_x \qquad (8)$$

$$\frac{dM_y}{dt} = \gamma_F(M_z B_x - M_x B_z) - \Gamma_0 M_y - \Gamma_p(M_p - M_y) \qquad (9)$$

$$\frac{dM_z}{dt} = \gamma_F(M_x B_y - M_y B_x) - \Gamma_0 M_z - \Gamma_p M_z \qquad (10)$$

Since pumping light and probe light are applied to the gas cell 12 with constant power in a steady state, a steady solution of the spin polarization degree ($M_x$, $M_y$, $M_z$) can be obtained by setting the respective left sides of the above Equations 8 to 10 to zero. The solution can be obtained according to Equations 11 to 13.

$$M_x = \frac{c}{a} \cdot \frac{B_x B_y + aB_z}{a^2 + B_x^2 + B_y^2 + B_z^2} \qquad (11)$$

$$M_y = \frac{c}{a} \cdot \frac{a^2 + B_y^2}{a^2 + B_x^2 + B_y^2 + B_z^2} \qquad (12)$$

$$M_z = \frac{c}{a} \cdot \frac{B_y B_z - aB_x}{a^2 + B_x^2 + B_y^2 + B_z^2} \qquad (13)$$

In Equations 11 to 13, a and c are constants and are given by the following Equation 14.

$$a = \frac{\Gamma_0 + \Gamma_p}{\gamma_F} \quad c = \Gamma_p M_p \qquad (14)$$

(D) Measurement of Magnetic Field

Meanwhile, a case is assumed in which the artificial magnetic field A ($A_x$, $A_y$, $A_z$) is generated in the X axis direction, the Y axis direction, and the Z axis direction by the magnetic field generator 8 (8X, 8Y, and 8Z), and is applied to the gas cell 12. In this case, the magnetic field vector B ($B_x$, $B_y$, $B_z$) detected by the magnetic sensor 10 is a vector sum of the artificial magnetic field vector A ($A_x$, $A_y$, $A_z$) generated by the magnetic field generator 8 and the original magnetic field vector C ($C_x$, $C_y$, $C_z$) as shown in Equation 15. The original magnetic field C is a magnetic field which is present in the measurement region 5 when the artificial magnetic field A is zero.

$$\overline{B} = \overline{A} + \overline{C}(B_x, B_y, B_z) = (A_x + C_x, A_y + C_y, A_z + C_z) \qquad (15)$$

Here, the Z axis direction component $A_z$ of the artificial magnetic field vector A is set to zero ($A_z=0$). The X axis direction component $A_x$ of the artificial magnetic field vector A is set to a function $A_{10}f(t)$ having the amplitude $A_{10}$, and the Y axis direction component $A_y$ thereof is set to a function $A_{20}g(t)$ having the amplitude $A_{20}$. Therefore, the magnetic field vector B ($B_x$, $B_y$, $B_z$) detected by the magnetic sensor 10 in the measurement region 5 is expressed as in the following Equation 16. The amplitude $A_{10}$ and the amplitude $A_{20}$ are coefficients having dimensions of magnetic fields, and the function f(t) and the function g(t) are non-dimension functions.

$$\begin{pmatrix} B_x \\ B_y \\ B_z \end{pmatrix} = \begin{pmatrix} C_x + A_{10}f(t) \\ C_y + A_{20}g(t) \\ C_z \end{pmatrix} \quad (16)$$

If Equation 16 is assigned to the spin polarization degree $M_x$ of Equation 11, Equation 17 can be obtained.

$$M_x = \frac{c}{a} \cdot \frac{C_xC_y + C_xA_{20}g(t) + C_yA_{10}f(t) + A_{10}f(t)A_{20}g(t) + aC_z}{a^2 + C_x^2 + C_y^2 + C_z^2 + 2C_xA_{10}f(t) + 2C_yA_{20}g(t) + A_{10}^2f(t)^2 + A_{20}^2g(t)^2} \quad (17)$$

If $A_{10}=A_{20}=A_0$, control and computation are facilitated, and Equation 16 is expressed as in the following Equation 18.

$$\begin{pmatrix} B_x \\ B_y \\ B_z \end{pmatrix} = \begin{pmatrix} C_x + A_0f(t) \\ C_y + A_0g(t) \\ C_z \end{pmatrix} \quad (18)$$

If Equation 18 is assigned to the spin polarization degree $M_x$ of Equation 11, Equation 19 can be obtained.

$$M_x = \frac{c}{a} \cdot \frac{C_xC_y + C_xA_0g(t) + C_yA_0f(t) + A_0^2f(t)g(t) + aC_z}{a^2 + C_x^2 + C_y^2 + C_z^2 + 2C_xA_0f(t) + 2C_yA_0g(t) + A_0^2(f(t)^2 + g(t)^2)} \quad (19)$$

Three values of the respective components ($C_x$, $C_y$, $C_z$) of the original magnetic field vector C which are the unknowns are calculated as follows using Equation 19. That is, measurement is performed using the magnetic field measurement apparatus 1, and three or more combinations of a value $A_x(t)$ of the X axis direction component $A_x$ of the artificial magnetic field A and a value $A_y(t)$ of the Y axis direction component $A_y$ thereof generated by the magnetic field generator 8, and a spin polarization degree $M_x(t)$ (that is, an output value $W_-$ of the magnetic sensor 10) at a certain time point t and having different spin polarization degrees $M_x$ are acquired.

In addition, simultaneous equations defined by three equations which are obtained by assigning the artificial magnetic fields $A_x(t)$ and $A_y(t)$ and the spin polarization degree $M_x(t)$ to Equation 19 are generated for each combination. It is possible to calculate the respective components ($C_x$, $C_y$, $C_z$) of the original magnetic field vector C which are the unknowns by solving the simultaneous equations.

In Equation 19, the constants a and c may be the unknowns. In other words, Equation 19 contains five unknowns including the respective components ($C_x$, $C_y$, $C_z$) of the original magnetic field vector C, and the constants a and c. In this case, measurement is performed using the magnetic field measurement apparatus 1, and five combinations of the artificial magnetic fields $A_x(t)$ and $A_y(t)$ and the spin polarization degree $M_x(t)$ at a certain time point t and having different spin polarization degrees $M_x(t)$ are acquired. In addition, simultaneous equations defined by five equations which are obtained by assigning the respective values to Equation 19 are generated for each combination. It is possible to calculate the respective components ($C_x$, $C_y$, $C_z$) of the original magnetic field vector C, and the constants a and c, which are the unknowns by solving the simultaneous equations.

Further, six or more combinations of the artificial magnetic fields $A_x(t)$ and $A_y(t)$ and the spin polarization degree $M_x(t)$ and having different spin polarization degrees $M_x(t)$ may be acquired, and Equation 19 maybe fitted to the combinations. Specifically, the respective components ($C_x$, $C_y$, $C_z$) of the original magnetic field vector C, and the constants a and c, which are the unknowns, are calculated so that a deviation between the spin polarization degree $M_x$ calculated using Equation 19 and the measured value $M_x$ of the magnetic sensor 10 becomes the minimum.

If the amplitude $A_0$ of the time functions f(t) and g(t) set as the artificial magnetic fields $A_x$ and $A_y$ is sufficiently smaller than the X axis direction component $C_x$ and the Y axis direction component $C_y$ of the original magnetic field C (generally, 1/10 or less; $A_0<(C_x/10)$ and $A_0<(C_y/10)$), Equation 19 is simplified as Equation 20, and thus measurement is more easily performed.

$$M_x = \frac{c}{a} \cdot \frac{C_xC_y + C_xA_0g(t) + C_yA_0f(t) + aC_z}{a^2 + C_x^2 + C_y^2 + C_z^2 + 2C_xA_0f(t) + 2C_yA_0g(t)} \quad (20)$$

As mentioned above, the original magnetic field vector C ($C_x$, $C_y$, $C_z$) can be calculated on the basis of the artificial magnetic field A ($A_x$, $A_y$, $A_z$) generated by the magnetic field generator 8 and the spin polarization degree $M_x$ (that is, the square difference $W_-$) at that time using Equations 19 and 20.

(E) Artificial Magnetic Field A

The artificial magnetic field A ($A_x$, $A_y$, $A_z$) is defined as follows. In other words, the time function f(t) of the X axis direction component $A_x$ of the artificial magnetic field A takes fixed values $f_i$ (where i=1, . . . , and n) having n different levels, and the time function g(t) of the Y axis direction component $A_y$ of the artificial magnetic field A takes fixed values $g_j$ (where j=1, . . . , and m) having m different levels. Along therewith, the time functions f(t) and g(t) are defined so that a total of n×m measurement periods $\tau_k$ (where k=1, . . . , and n×m) corresponding to all combinations of the respective fixed values $f_i$ and $g_j$ of the time functions g(t) and f(t) are present.

In the present embodiment, as described above, it is necessary to acquire three or more combinations of the artificial magnetic fields $A_x(t)$ and $A_y(t)$ and the spin polarization degree $M_x(t)$ at a certain time point t and having different spin polarization degrees $M_x(t)$ in order to calculate the respective components ($C_x$, $C_y$, $C_z$) of the original magnetic field vector C. In other words, it is necessary to define the fixed values $f_i$ and $g_j$ taken by the respective time functions g(t) and f(t) so that three or more measurement periods τk (where k≥3) are present.

The spin polarization degree $M_x$ in the measurement periods τk corresponding to the combinations of the respective fixed values $f_i$ and $g_j$ of the time functions f(t) and g(t) of the artificial magnetic fields $A_x$ and $A_y$ are expressed as in the following Equations 21 and 22 from Equations 19 and 20, respectively. Herein, the spin polarization degree $M_x(t)$ is indicated by $M_{xij}$ when $f(t)=f_i$, and $g(t)=g_j$.

$$M_{xij} = \frac{c}{a} \cdot \frac{C_x C_y + C_x A_{20} g_j + C_y A_{10} f_i + A_{10} f_i A_{20} g_j + aC_z}{a^2 + C_x^2 + C_y^2 + C_z^2 + 2C_x A_{10} f_i + 2C_y A_{20} g_j + (A_{10} f_i)^2 + (A_{20} g_j)^2} \quad (21)$$

$$M_{xij} = \frac{c}{a} \cdot \frac{C_x C_y + C_x A_{20} g_j + C_y A_{10} f_i + aC_z}{a^2 + C_x^2 + C_y^2 + C_z^2 + 2C_x A_{10} f_i + 2C_y A_{20} g_j} \quad (22)$$

The unknowns are three coefficients including $C_x$, $C_y$, and $C_z$, and thus three or more $M_{xij}$ are measured. Therefore, in order to change both of the X side and the Y side, a total of four or more $M_{xij}$ are measured at n of an integer of 2 or greater and m of an integer of 2 or greater. If only the X side is to be changed, three or more $M_{xij}$ are measured at n of an integer of 3 or greater. If only the Y side is to be changed, three or more $M_{xij}$ are measured at m of an integer of 3 or greater.

In a case where the constants a and c are set as the unknowns, five unknowns are present, and thus three or more $M_{xij}$ are measured. Therefore, if both of the X side and the Y side are to be changed, a total of six or more $M_{xij}$ are measured at one of n and m of an integer of 2 or greater and the other of an integer of 3 or greater. If only the X side is to be changed, five or more $M_{xij}$ are measured at n of an integer of 5 or greater. If only the Y side is to be changed, five or more $M_{xij}$ are measured at m of an integer of 5 or greater.

In the same manner as in the previous case, if $A_{10}=A_{20}=A_0$, control and computation are facilitated, and Equations 21 and 22 are respectively expressed as in the following Equations 23 and 24.

$$M_{xij} = \frac{c}{a} \cdot \frac{C_x C_y + C_x A_0 g_j + C_y A_0 f_i + A_0 f_i A_0 g_j + aC_z}{a^2 + C_x^2 + C_y^2 + C_z^2 + 2C_x A_0 f_i + 2C_y A_0 g_j + (A_0 f_i)^2 + (A_0 g_j)^2} \quad (23)$$

$$M_{xij} = \frac{c}{a} \cdot \frac{C_x C_y + C_x A_0 g_j + C_y A_0 f_i + aC_z}{a^2 + C_x^2 + C_y^2 + C_z^2 + 2C_x A_0 f_i + 2C_y A_0 g_j} \quad (24)$$

Flow of Process

Figure 13:
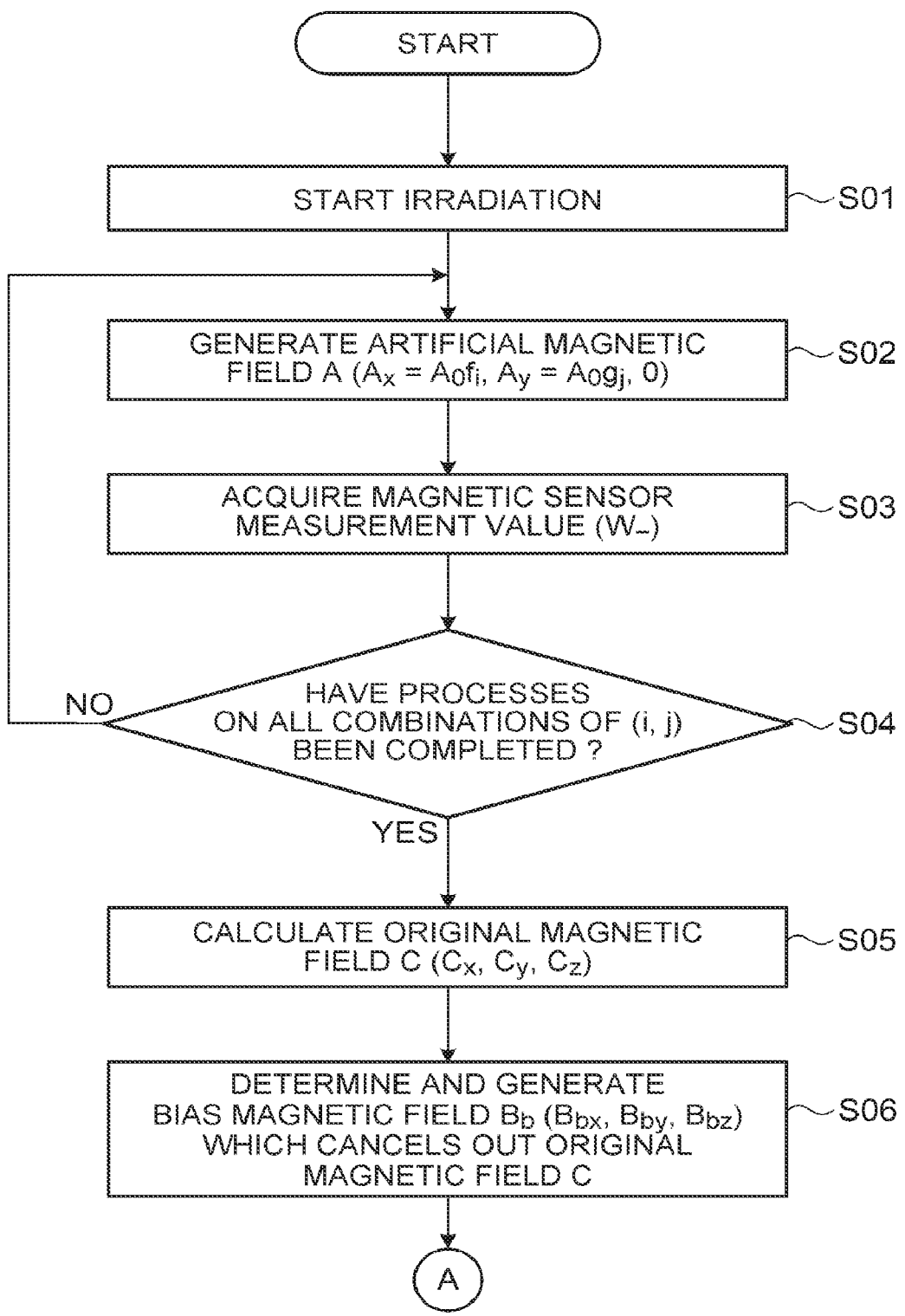
FIG. 13 is a flowchart illustrating a flow of a magnetic field measurement process according to the present embodiment.
Figure 14:
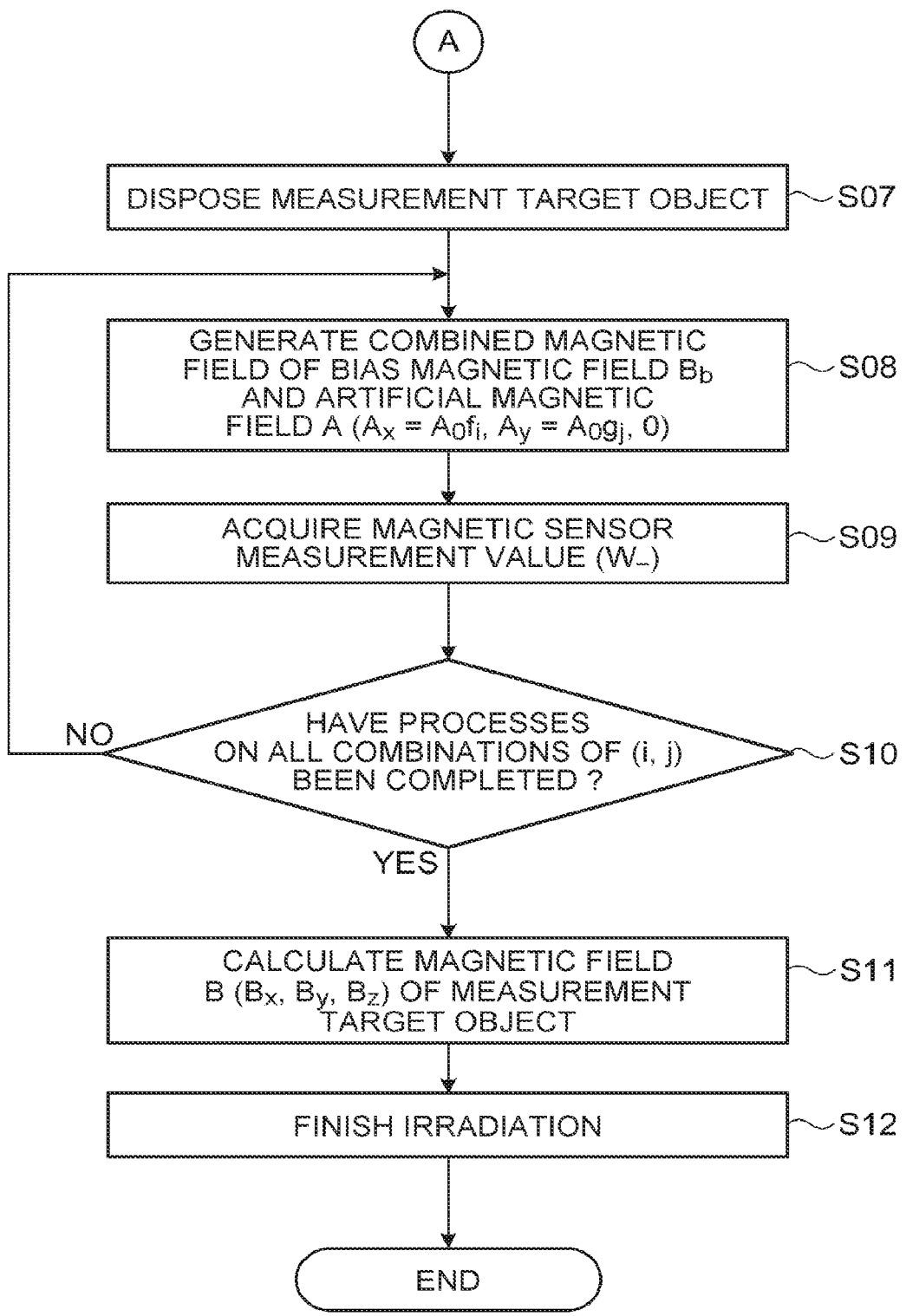
FIG. 14 is a flowchart illustrating a flow of the magnetic field measurement process according to the present embodiment.

FIGS. 13 and 14 are flowcharts illustrating a flow of a magnetic field measurement process according to the present embodiment. This process is a process which is realized by each portion of the processing unit 40 illustrated in FIG. 7 executing the magnetic field measurement program 51. As an example, a description will be made of a case where a measurement target object is the human body (subject 9), and a heart magnetic field (a magnetic field generated due to electrophysiological activity of the heart) or a brain magnetic field is measured.

As illustrated in FIG. 13, first, the irradiation control portion 41 causes the light source 18 to start irradiation with irradiation light including linearly polarized light components which serve as pump light and probe light (step S01).

Thereafter, the original magnetic field C is measured. Specifically, the magnetic field generation control portion 42 causes the magnetic field generator 8 to generate the artificial magnetic field A ($A_x=A_0 f_i$, $A_y=A_0 g_j$, 0) corresponding to a target combination (i, j) (step S02). In this state, a measurement value (square difference W_) obtained on the basis of a signal output from the magnetic sensor 10 is acquired (step S03).

The processes in steps S02 and S03 are repeatedly performed on each of combinations of numbers i (where i=1 to n) of the fixed value f of the time function f(t) as the X axis direction component $A_x$ of the artificial magnetic field and numbers j (where j=1 to m) of the fixed value g of the time function g(t) as the Y axis direction component $A_y$ (step S04). In other words, in a case where the processes on all combinations of (i, j) are not completed (NO in step S04), the processes in steps S02 and S03 are performed on combinations of (i, j) on which the processes have not been performed yet.

If the processes in steps S02 and S03 on all of the combinations of (i, j) are completed (YES in step S04), the original magnetic field calculation portion 43 calculates the original magnetic field vector C ($C_x$, $C_y$, $C_z$) using combinations of the artificial magnetic fields $A_x$ and $A_y$ and the acquired measurement values (the square difference W_) (step S05). Next, the bias magnetic field determination portion 44 determines the bias magnetic field $B_b$ which cancels out the calculated original magnetic field C (step S06).

Next, as illustrated in FIG. 14, the measurement target object is disposed to be close to the magnetic sensor 10 (step S07). The magnetic field B generated by the measurement target object is measured. Specifically, the magnetic field generation control portion 42 causes the magnetic field generator 8 to generate a combined magnetic field of the artificial magnetic field A ($A_x=A_0 f_i$, $A_y=A_0 g_j$, 0) corresponding to the target combination (i, j) and the bias magnetic field $B_b$ (step S08). In this state, a measurement value (the square difference W_) obtained on the basis of a signal output from the magnetic sensor 10 is acquired (step S09).

The processes in steps S08 and S09 are repeatedly performed on each of combinations of numbers i (where i=1 to n) of the fixed value f of the time function f(t) as the X axis direction component $A_x$ of the artificial magnetic field and numbers j (where j=1 to m) of the fixed value g of the time function g(t) as the Y axis direction component $A_y$ (step S10). In other words, in a case where the processes on all combinations of (i, j) are not completed (NO in step S10), the processes in steps S08 and S09 are performed on combinations of (i, j) on which the processes have not been performed yet.

If the processes in steps S08 and S09 on all of the combinations of (i, j) are completed (YES in step S10), the target magnetic field calculation portion 45 calculates the magnetic field B ($B_x$, $B_y$, $B_z$) generated by the measurement target object using combinations of the artificial magnetic fields $A_x$ and $A_y$ and the acquired measurement values (the square difference W_) (step S11). Thereafter, the irradiation control portion 41 causes the light source 18 to finish the irradiation with the irradiation light (step S12). If the above-described processes are performed, the processing unit 40 finishes the magnetism measurement process.

As specific Examples in the magnetic field measurement apparatus 1 with the above-described configuration, three Examples for specifically describing the artificial magnetic field A ($A_x$, $A_y$, $A_z$) will now be described.

Example 1

Example 1 is an example in which the time function f(t) set as the X axis direction component $A_x$ of the artificial magnetic field A takes two fixed values $f_1$ and $f_2$ (corresponding to Application Example 9). In Example 1, at least one of the two fixed values $f_1$ and $f_2$ is zero, the time function g(t) set as the Y axis direction component $A_y$ of the artificial magnetic field A takes two fixed values $g_1$ and $g_2$, and at least one of the two fixed values $g_1$ and $g_2$ is zero.

Figure 15:
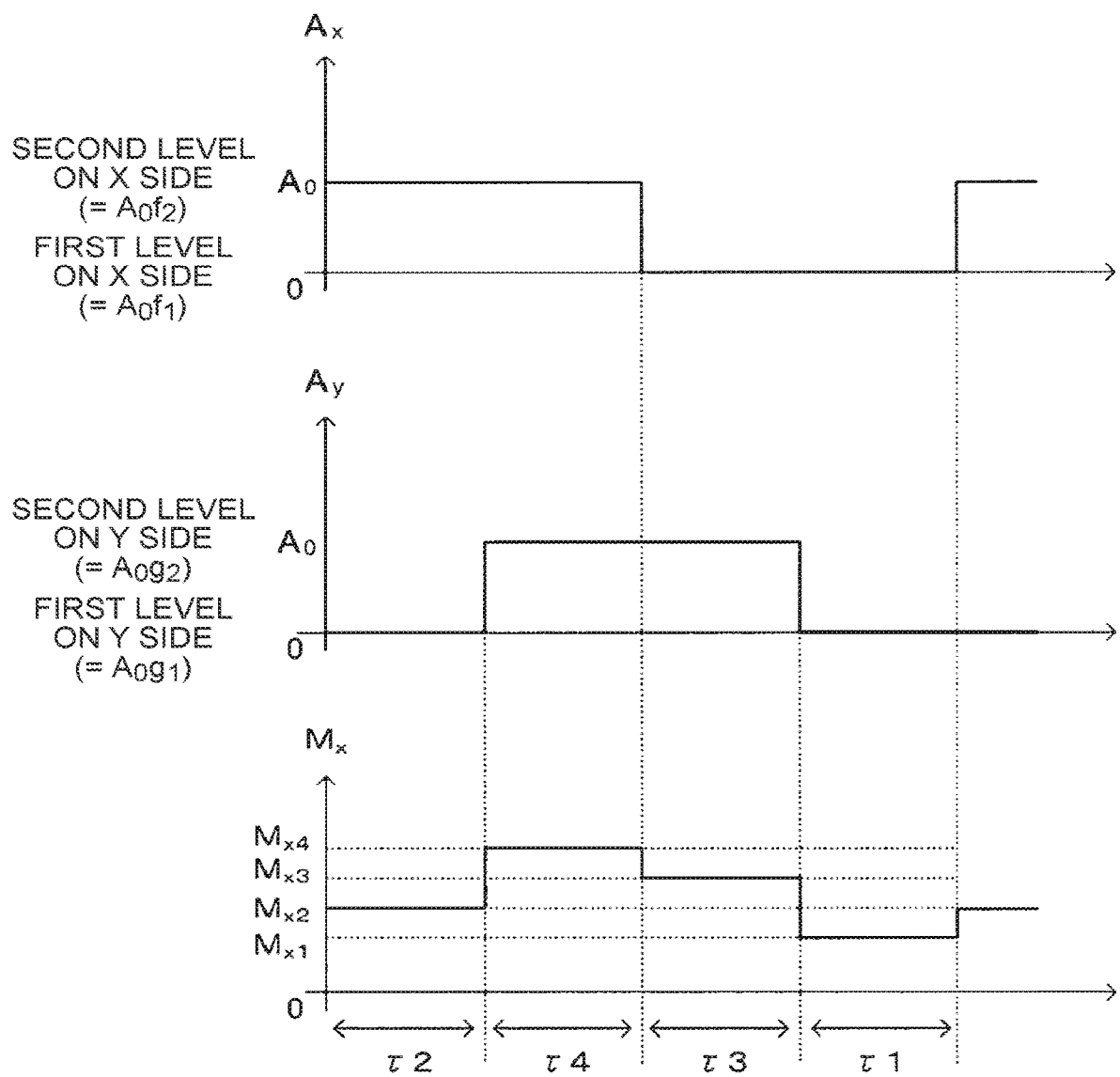
FIG. 15 shows graphs illustrating examples of artificial magnetic fields $A_x$ and $A_y$ and a spin polarization degree $M_x$ in Example 1.

FIG. 15 shows graphs illustrating examples of the artificial magnetic fields $A_x$ and $A_y$ and the spin polarization degree $M_x$ in Example 1. FIG. 15 shows graphs of the artificial magnetic fields $A_x$ and $A_y$ and the spin polarization degree $M_x$ in this order from the top, in which transverse axes thereof express a common time point t.

The time function f(t) takes $f_1=0$ and $f_2=1$ as the fixed value $f_i$, and the time function g(t) takes $g_1=0$ and $g_2=1$ as the fixed value $g_j$. Therefore, the X axis direction component $A_x$ of the artificial magnetic field A takes two values including "$A_0 f_1=0$" which is a constant magnetic field with a first level on the X side and "$A_0 f_2=A_0$" which is a constant magnetic field with a second level on the X side. The Y axis direction component $A_y$ takes two values including "$A_0 g_1=0$" which is a constant magnetic field with a first level on the Y side and "$A_0 g_2=A_0$" which is a constant magnetic field with a second level on the Y side.

Four measurement periods $\tau 1$ to $\tau 4$ corresponding to all combinations of the fixed values $f_1$ and $f_2$ of the time function f(t) and the fixed values $g_1$ and $g_2$ of the time function g(t) are present. Spin polarization degrees $M_{x1}$ to $M_{x4}$ in the respective measurement periods $\tau 1$ to $\tau 4$ are different from each other. In other words, it is possible to acquire three or more combinations of constant magnetic fields with an i-th level (where i=1 and 2) on the X side as the X axis direction component $A_x$ of the artificial magnetic field A and constant magnetic fields with a j-th level (where j=1 and 2) on the Y side as the Y axis direction component $A_y$, and the spin polarization degrees $M_x$ as magnetization values, which are necessary to calculate the original magnetic field vector C ($C_x$, $C_y$, $C_z$) using Equation 19, and having different spin polarization degrees $M_x$.

Specifically, a time function is $f(\tau 1)=f_1=0$, and a time function is $g(\tau 1)=g_1=0$ in the first measurement period $\tau 1$ in which i=j=1. In other words, the constant magnetic field with the first level on the X side is generated as the X axis direction component $A_x$ of the artificial magnetic field A, and the constant magnetic field with the first level on the Y side is generated as the Y axis direction component $A_y$. Therefore, Equation 16 related to the magnetic field B applied to the gas cell 12 is expressed as in the following Equation 25.

$$\begin{pmatrix} B_x \\ B_y \\ B_z \end{pmatrix} = \begin{pmatrix} C_x \\ C_y \\ C_z \end{pmatrix} \quad (25)$$

Equation 23 related to the spin polarization degree $M_x$ which is a (1-1)-th magnetization value is expressed as in the following Equation 26.

$$M_{x1} = \frac{c}{a} \cdot \frac{C_x C_y + a C_z}{a^2 + C_x^2 + C_y^2 + C_z^2} \quad (26)$$

In addition, a time function is $f(\tau 2)=f_2=1$, and a time function is $g(\tau 2)=g_1=0$ in the second measurement period $\tau 2$ in which i=2 and j=1. In other words, a constant magnetic field with a second level on the X side is generated as the X axis direction component $A_x$ of the artificial magnetic field A, and the constant magnetic field with the first level on the Y side is generated as the Y axis direction component $A_y$. Therefore, Equation 16 related to the magnetic field B applied to the gas cell 12 is expressed as in the following Equation 27.

$$\begin{pmatrix} B_x \\ B_y \\ B_z \end{pmatrix} = \begin{pmatrix} C_x + A_0 \\ C_y \\ C_z \end{pmatrix} \quad (27)$$

Equation 23 related to the spin polarization degree $M_x$ which is a (2-1)-th magnetization value is expressed as in the following Equation 28.

$$M_{x2} = \frac{c}{a} \cdot \frac{C_x C_y + C_y A_0 + a C_z}{a^2 + C_x^2 + C_y^2 + C_z^2 + 2 C_x A_0 + A_0^2} \quad (28)$$

In addition, a time function is $f(\tau 3)=f_1=0$, and a time function is $g(\tau 3)=g_2=1$ in the third measurement period $\tau 3$ in which i=1 and j=2. In other words, the constant magnetic field with the first level on the X side is generated as the X axis direction component $A_x$ of the artificial magnetic field A, and a constant magnetic field with a second level on the Y side is generated as the Y axis direction component $A_y$. Therefore, Equation 16 related to the magnetic field B applied to the gas cell 12 is expressed as in the following Equation 29.

$$\begin{pmatrix} B_x \\ B_y \\ B_z \end{pmatrix} = \begin{pmatrix} C_x \\ C_y + A_0 \\ C_z \end{pmatrix} \quad (29)$$

Equation 23 related to the spin polarization degree $M_x$ which is a (1-2)-th magnetization value is expressed as in the following Equation 30.

$$M_{x3} = \frac{c}{a} \cdot \frac{C_x C_y + C_x A_0 + a C_z}{a^2 + C_x^2 + C_y^2 + C_z^2 + 2 C_y A_0 + A_0^2} \quad (30)$$

In addition, a time function is $f(\tau 4)=f_2=1$, and a time function is $g(\tau 4)=g_2=1$ in the fourth measurement period $\tau 4$ in which i=j=2. In other words, the constant magnetic field with the second level on the X side is generated as the X axis direction component $A_x$ of the artificial magnetic field A, and the constant magnetic field with the second level on the Y side is generated as the Y axis direction component $A_y$. Therefore, Equation 16 related to the magnetic field B applied to the gas cell 12 is expressed as in the following Equation 31.

$$\begin{pmatrix} B_x \\ B_y \\ B_z \end{pmatrix} = \begin{pmatrix} C_x + A_0 \\ C_y + A_0 \\ C_z \end{pmatrix} \quad (31)$$

Equation 23 related to the spin polarization degree $M_x$ which is a (2-2)-th magnetization value is expressed as in the following Equation 32.

$$M_{x4} = \frac{c}{a} \cdot \frac{C_x C_y + C_x A_0 + C_y A_0 + A_0^2 + aC_z}{a^2 + C_x^2 + C_y^2 + C_z^2 + 2C_x A_0 + 2C_y A_0 + 2A_0^2} \quad (32)$$

A first equation is obtained by assigning the magnetization value ($M_{x1}$) obtained from the magnetic field measurement apparatus 1 in the first measurement period τ1 to the left side of Equation 26. A second equation is obtained by assigning the magnetization value ($M_{x2}$) obtained from the magnetic field measurement apparatus 1 in the second measurement period τ2 to the left side of Equation 28. A third equation is obtained by assigning the magnetization value ($M_{x3}$) obtained from the magnetic field measurement apparatus 1 in the third measurement period τ3 to the left side of Equation 30. A fourth equation is obtained by assigning the magnetization value ($M_{x4}$) obtained from the magnetic field measurement apparatus 1 in the fourth measurement period τ4 to the left side of Equation 32. In addition, simultaneous equations containing the four equations are solved in order to calculate the original magnetic field vector C ($C_x$, $C_y$, $C_z$) as the unknowns.

Example 2

Example 2 is an example in which the time function f(t) set as the X axis direction component $A_x$ of the artificial magnetic field A takes three fixed values $f_1$, $f_2$, and $f_3$. In Example 2, at least one of the three fixed values $f_1$, $f_2$, and $f_3$ is zero, the time function g(t) set as the Y axis direction component $A_y$ of the artificial magnetic field A takes three fixed values $g_1$, $g_2$, and $g_3$, and at least one of the three fixed values $g_1$, $g_2$, and $g_3$ is zero.

Figure 16:
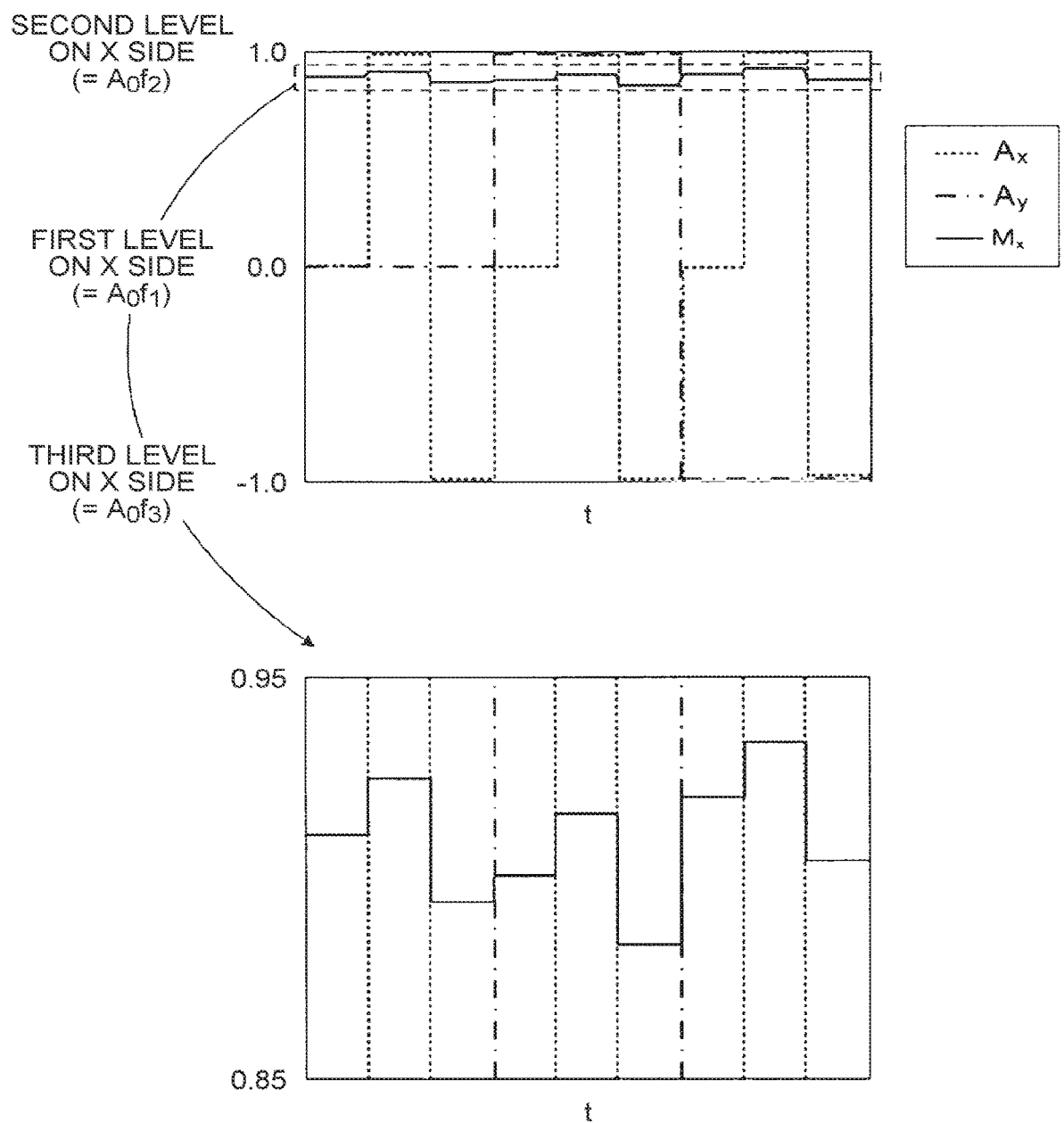
FIG. 16 shows graphs illustrating examples of artificial magnetic fields $A_x$ and $A_y$ and a spin polarization degree $M_x$ in Example 2.

FIG. 16 shows graphs illustrating examples of the artificial magnetic fields $A_x$ and $A_y$ and the spin polarization degree $M_x$ in Example 2. FIG. 16 shows graphs of the artificial magnetic fields $A_x$ and $A_y$ and the spin polarization degree $M_x$ in this order from the top, in which transverse axes thereof express a time point t. The lower drawing vertically enlarges and illustrates a part of the upper graph for better understanding of a change in the spin polarization degree $M_x$.

The time function f(t) takes $f_1=0$, $f_2=1$, and $f_3=-1$ as the fixed value $f_i$, and the time function g(t) takes $g_1=0$, $g_2=1$, and $g_3=-1$ as the fixed value $g_j$. Therefore, each of the artificial magnetic fields $A_x$ and $A_y$ has three values (0, $A_0$, $-A_0$). Nine measurement periods τ1 to τ9 corresponding to all combinations of the fixed values $f_1$ to $f_3$ of the time function f(t) and the fixed values $g_1$ to $g_3$ of the time function g(t) are present.

Spin polarization degrees $M_{x1}$ to $M_{x9}$ in the respective measurement periods τ1 to τ9 are different from each other. In other words, it is possible to acquire three or more combinations of the artificial magnetic fields $A_x$ and $A_y$ and the spin polarization degrees $M_x$, which are necessary to calculate the original magnetic field vector C ($C_x$, $C_y$, $C_z$) using Equation 19, and having different spin polarization degrees $M_x$.

Specifically, a time function is $f(\tau 1)=f_1=0$, and a time function is $g(\tau 1)=g_1=0$ in the first measurement period τ1 in which i=j=1. Therefore, Equation 16 related to the magnetic field B applied to the gas cell 12 is expressed as in the following Equation 33.

$$\begin{pmatrix} B_x \\ B_y \\ B_z \end{pmatrix} = \begin{pmatrix} C_x \\ C_y \\ C_z \end{pmatrix} \quad (33)$$

Equation 23 related to the spin polarization degree $M_x$ is expressed as in the following Equation 34.

$$M_{x1} = \frac{c}{a} \cdot \frac{C_x C_y + aC_z}{a^2 + C_x^2 + C_y^2 + C_z^2} \quad (34)$$

In addition, a time function is $f(\tau 2)=f_2=1$, and a time function is $g(\tau 2)=g_1=0$ in the second measurement period τ2 in which i=2 and j=1. Therefore, Equation 16 related to the magnetic field B applied to the gas cell 12 is expressed as in the following Equation 35.

$$\begin{pmatrix} B_x \\ B_y \\ B_z \end{pmatrix} = \begin{pmatrix} C_x + A_0 \\ C_y \\ C_z \end{pmatrix} \quad (35)$$

Equation 23 related to the spin polarization degree $M_x$ is expressed as in the following Equation 36.

$$M_{x2} = \frac{c}{a} \cdot \frac{C_x C_y + C_y A_0 + aC_z}{a^2 + C_x^2 + C_y^2 + C_z^2 + 2C_x A_0 + A_0^2} \quad (36)$$

In addition, a time function is $f(\tau 3)=f_3=-1$, and a time function is $g(\tau 3)=g_1=0$ in the third measurement period τ3 in which i=3 and j=1. Therefore, Equation 16 related to the magnetic field B applied to the gas cell 12 is expressed as in the following Equation 37.

$$\begin{pmatrix} B_x \\ B_y \\ B_z \end{pmatrix} = \begin{pmatrix} C_x - A_0 \\ C_y \\ C_z \end{pmatrix} \quad (37)$$

Equation 23 related to the spin polarization degree $M_x$ is expressed as in the following Equation 38.

$$M_{x3} = \frac{c}{a} \cdot \frac{C_x C_y - C_y A_0 + aC_z}{a^2 + C_x^2 + C_y^2 + C_z^2 - 2C_x A_0 + A_0^2} \quad (38)$$

In addition, a time function is $f(\tau 4)=f_1=0$, and a time function is $g(\tau 4)=g_2=1$ in the fourth measurement period τ4 in which i=1 and j=2. Therefore, Equation 16 related to the magnetic field B applied to the gas cell 12 is expressed as in the following Equation 39.

$$\begin{pmatrix} B_x \\ B_y \\ B_z \end{pmatrix} = \begin{pmatrix} C_x \\ C_y + A_0 \\ C_z \end{pmatrix} \qquad (39)$$

Equation 23 related to the spin polarization degree $M_x$ is expressed as in the following Equation 40.

$$M_{x4} = \frac{c}{a} \cdot \frac{C_x C_y + C_x A_0 + aC_z}{a^2 + C_x^2 + C_y^2 + C_z^2 + 2C_y A_0 + A_0^2} \qquad (40)$$

In addition, a time function is $f(\tau 5)=f_2=1$, and a time function is $g(\tau 5)=g_2=1$ in the fifth measurement period $\tau 5$ in which $i=j=2$. Therefore, Equation 16 related to the magnetic field B applied to the gas cell 12 is expressed as in the following Equation 41.

$$\begin{pmatrix} B_x \\ B_y \\ B_z \end{pmatrix} = \begin{pmatrix} C_x + A_0 \\ C_y + A_0 \\ C_z \end{pmatrix} \qquad (41)$$

Equation 23 related to the spin polarization degree $M_x$ is expressed as in the following Equation 42.

$$M_{x5} = \frac{c}{a} \cdot \frac{C_x C_y + C_x A_0 + C_y A_0 + A_0^2 + aC_z}{a^2 + C_x^2 + C_y^2 + C_z^2 + 2C_x A_0 + 2C_y A_0 + A_0^2} \qquad (42)$$

In addition, a time function is $f(\tau 6)=f_3=-1$, and a time function is $g(\tau 6)=g_2=1$ in the sixth measurement period $\tau 6$ in which $i=3$ and $j=2$. Therefore, Equation 16 related to the magnetic field B applied to the gas cell 12 is expressed as in the following Equation 43.

$$\begin{pmatrix} B_x \\ B_y \\ B_z \end{pmatrix} = \begin{pmatrix} C_x - A_0 \\ C_y + A_0 \\ C_z \end{pmatrix} \qquad (43)$$

Equation 23 related to the spin polarization degree $M_x$ is expressed as in the following Equation 44.

$$M_{x6} = \frac{c}{a} \cdot \frac{C_x C_y + C_x A_0 - C_y A_0 - A_0^2 + aC_z}{a^2 + C_x^2 + C_y^2 + C_z^2 - 2C_x A_0 + 2C_y A_0 + 2A_0^2} \qquad (44)$$

In addition, a time function is $f(\tau 7)=f_1=0$, and a time function is $g(\tau 7)=g_3=-1$ in the seventh measurement period $\tau 7$ in which $i=1$ and $j=3$. Therefore, Equation 16 related to the magnetic field B applied to the gas cell 12 is expressed as in the following Equation 45.

$$\begin{pmatrix} B_x \\ B_y \\ B_z \end{pmatrix} = \begin{pmatrix} C_x \\ C_y - A_0 \\ C_z \end{pmatrix} \qquad (45)$$

Equation 23 related to the spin polarization degree $M_x$ is expressed as in the following Equation 46.

$$M_{x6} = \frac{c}{a} \cdot \frac{C_x C_y - C_x A_0 + aC_z}{a^2 + C_x^2 + C_y^2 + C_z^2 - 2C_y A_0 + A_0^2} \qquad (46)$$

In addition, a time function is $f(\tau 8)=f_2=1$, and a time function is $g(\tau 8)=g_3=-1$ in the eighth measurement period $\tau 8$ in which $i=2$ and $j=3$. Therefore, Equation 16 related to the magnetic field B applied to the gas cell 12 is expressed as in the following Equation 47.

$$\begin{pmatrix} B_x \\ B_y \\ B_z \end{pmatrix} = \begin{pmatrix} C_x + A_0 \\ C_y - A_0 \\ C_z \end{pmatrix} \qquad (47)$$

Equation 23 related to the spin polarization degree $M_x$ is expressed as in the following Equation 48.

$$M_{x8} = \frac{c}{a} \cdot \frac{C_x C_y - C_x A_0 + C_y A_0 - A_0^2 + aC_z}{a^2 + C_x^2 + C_y^2 + C_z^2 + 2C_x A_0 - 2C_y A_0 + 2A_0^2} \qquad (48)$$

In addition, a time function is $f(\tau 9)=f_3=-1$, and a time function is $g(\tau 9)=g_3=-1$ in the ninth measurement period $\tau 9$ in which $i=j=3$. Therefore, Equation 16 related to the magnetic field B applied to the gas cell 12 is expressed as in the following Equation 49.

$$\begin{pmatrix} B_x \\ B_y \\ B_z \end{pmatrix} = \begin{pmatrix} C_x - A_0 \\ C_y - A_0 \\ C_z \end{pmatrix} \qquad (49)$$

Equation 23 related to the spin polarization degree $M_x$ is expressed as in the following Equation 50.

$$M_{x9} = \frac{c}{a} \cdot \frac{C_x C_y - C_x A_0 - C_y A_0 + A_0^2 + aC_z}{a^2 + C_x^2 + C_y^2 + C_z^2 - 2C_x A_0 - 2C_y A_0 + 2A_0^2} \qquad (50)$$

A first equation is obtained by assigning the magnetization value ($M_{x1}$) obtained from the magnetic field measurement apparatus 1 in the first measurement period $\tau 1$ to the left side of Equation 34. A second equation is obtained by assigning the magnetization value ($M_{x2}$) obtained from the magnetic field measurement apparatus 1 in the second measurement period $\tau 2$ to the left side of Equation 36. A third equation is obtained by assigning the magnetization value ($M_{x3}$) obtained from the magnetic field measurement apparatus 1 in the third measurement period $\tau 3$ to the left side of Equation 38.

A fourth equation is obtained by assigning the magnetization value ($M_{x4}$) obtained from the magnetic field measurement apparatus 1 in the fourth measurement period $\tau 4$ to the left side of Equation 40. A fifth equation is obtained by assigning the magnetization value ($M_{x5}$) obtained from the magnetic field measurement apparatus 1 in the fifth measurement period $\tau 5$ to the left side of Equation 42. A sixth equation is obtained by assigning the magnetization value ($M_{x6}$) obtained from the magnetic field measurement apparatus 1 in the sixth measurement period $\tau 6$ to the left side of Equation 44.

A seventh equation is obtained by assigning the magnetization value ($M_{x7}$) obtained from the magnetic field measurement apparatus 1 in the seventh measurement period $\tau 7$ to the left side of Equation 46. An eighth equation is obtained by assigning the magnetization value ($M_{x8}$) obtained from the magnetic field measurement apparatus 1 in the eighth measurement period $\tau 8$ to the left side of Equation 48. A ninth equation is obtained by assigning the magnetization value ($M_{x9}$) obtained from the magnetic field measurement apparatus 1 in the ninth measurement period $\tau 9$ to the left side of Equation 50. In addition, simultaneous equations containing the nine equations are solved in order to calculate the original magnetic field vector C ($C_x$, $C_y$, $C_z$) as the unknowns.

Example 3

Example 3 is an example in which only a single axis direction component (X axis direction component) is generated and applied as the artificial magnetic field A (corresponding to Application Example 2). In other words, this corresponds to a case where g(t) is set to 0 in Equation 17 related to the spin polarization degree $M_x$. The time function f(t) set as the X axis direction component $A_x$ of the artificial magnetic field A takes three fixed values $f_1$, $f_2$, and $f_3$, and one of the three fixed values $f_1$, $f_2$, and $f_3$ is zero.

In other words, the X axis direction component $A_x$ of the artificial magnetic field A takes three values including "$A_0f_1=0$" which is a constant magnetic field with a first level on the X side, "$A_0f_2=A_0$" which is a constant magnetic field with a second level on the X side, and "$A_0f_3=-A_0$" which is a constant magnetic field with a third level on the X side. Thus, Equations 21 and 22 related to the spin polarization degree $M_x$ are respectively expressed as in the following Equations 51 and 52.

$$M_{xi} = \frac{c}{a} \cdot \frac{C_x C_y + C_y A_{10} f_i + aC_z}{a^2 + C_x^2 + C_y^2 + C_z^2 + 2C_y A_{10} f_i + (A_{10} f_i)^2} \quad (51)$$

$$M_{zi} = \frac{c}{a} \cdot \frac{C_x C_y + C_y A_{10} f_i + aC_z}{a^2 + C_x^2 + C_y^2 + C_z^2 + 2C_y A_{10} f_i} \quad (52)$$

In this case, three measurement periods $\tau 1$ to $\tau 3$ corresponding to the fixed values $f_1$ to $f_3$ of the artificial magnetic field A are present. For example, the time function f(t) takes $f_1=0$, $f_2=1$, and $f_3=-1$ as the fixed value $f_i$. Then, the three measurement periods $\tau 1$ to $\tau 3$ are the same as the measurement periods $\tau 1$ to $\tau 3$ in the above Example 2.

In other words, the constant magnetic field with the first level on the X side is generated as the X axis direction component $A_x$ of the artificial magnetic field A in the first measurement period $\tau 1$ in which i=1 and j=1 ($g_1=0$). The magnetic field B applied to the gas cell 12 is expressed as in Equation 33, and the spin polarization degree $M_x$ which is a (1-1)-th magnetization value is expressed as in Equation 34.

In addition, a constant magnetic field with a second level on the X side is generated as the X axis direction component $A_x$ of the artificial magnetic field A in the second measurement period $\tau 2$ in which i=2 and j=1 ($g_1=0$). The magnetic field B applied to the gas cell 12 is expressed as in Equation 35, and the spin polarization degree $M_x$ which is a (2-1)-th magnetization value is expressed as in Equation 36.

Further, a constant magnetic field with a third level on the X side is generated as the X axis direction component $A_x$ of the artificial magnetic field A in the third measurement period $\tau 3$ in which i=3 and j=1 ($g_1=0$). The magnetic field B applied to the gas cell 12 is expressed as in Equation 37, and the spin polarization degree $M_x$ which is a (3-1)-th magnetization value is expressed as in Equation 38.

As mentioned above, the spin polarization degrees $M_x$ in the respective measurement periods $\tau 1$ to $\tau 3$ are different from each other. Therefore, it is possible to acquire three or more combinations of the artificial magnetic fields $A_x$ and $A_y$, and the spin polarization degrees $M_x$, which are necessary to calculate the original magnetic field vector C ($C_x$, $C_y$, $C_z$) using Equation 17, and having different spin polarization degrees $M_x$.

Example 4

Example 4 is an example in which only a single axis direction component (Y axis direction component) is generated and applied as the artificial magnetic field A (corresponding to Application Example 6). In other words, this corresponds to a case where f(t) is set to 0 in Equation 17 related to the spin polarization degree $M_x$. The time function g(t) set as the Y axis direction component $A_y$ of the artificial magnetic field A takes three fixed values $g_1$, $g_2$, and $g_3$, and one of the three fixed values $g_1$, $g_2$, and $g_3$ is zero.

In other words, the Y axis direction component $A_y$ of the artificial magnetic field A takes three values including "$A_0g_1=0$" which is a constant magnetic field with a first level on the Y side, "$A_0g_2=A_0$" which is a constant magnetic field with a second level on the Y side, and "$A_0g_3=-A_0$" which is a constant magnetic field with a third level on the Y side. Thus, Equations 21 and 22 related to the spin polarization degree $M_x$ are respectively expressed as in the following Equations 53 and 54.

$$M_{xj} = \frac{c}{a} \cdot \frac{C_x C_y + C_x A_{20} g_j + aC_z}{a^2 + C_x^2 + C_y^2 + C_z^2 + 2C_y A_{20} g_j + (A_{20} g_j)^2} \quad (53)$$

$$M_{zj} = \frac{c}{a} \cdot \frac{C_x C_y + C_x A_{20} g_j + aC_z}{a^2 + C_x^2 + C_y^2 + C_z^2 + 2C_y A_{20} g_j} \quad (54)$$

In this case, three measurement periods $\tau 1$ to $\tau 3$ corresponding to the fixed values $g_1$ to $g_3$ of the artificial magnetic field A are present. For example, the time function g(t) takes $g_1=0$, $g_2=1$, and $g_3=-1$ as the fixed value $g_j$. Then, the three measurement periods $\tau 1$ to $\tau 3$ are the same as the measurement periods $\tau 1$ to $\tau 3$ in the above Example 2.

In other words, the constant magnetic field with the first level on the Y side is generated as the Y axis direction component $A_y$ of the artificial magnetic field A in the first measurement period $\tau 1$ in which i=1 ($f_1=0$) and j=1. The magnetic field B applied to the gas cell 12 is expressed as in Equation 33, and the spin polarization degree $M_x$ which is a (1-1)-th magnetization value is expressed as in Equation 34.

In addition, the constant magnetic field with the second level on the Y side is generated as the Y axis direction component $A_y$ of the artificial magnetic field A in the second measurement period $\tau 2$ in which i=1 ($f_1=0$) and j=2. The magnetic field B applied to the gas cell 12 is expressed as in Equation 39, and the spin polarization degree $M_x$ which is a (1-2)-th magnetization value is expressed as in Equation 40.

Further, the constant magnetic field with the third level on the Y side is generated as the Y axis direction component $A_y$ of the artificial magnetic field A in the third measurement period $\tau 3$ in which i=1 ($f_1=0$) and j=3. The magnetic field B applied to the gas cell 12 is expressed as in Equation 45, and the spin polarization degree $M_x$ which is a (1-3)-th magnetization value is expressed as in Equation 46.

As mentioned above, the spin polarization degrees $M_x$ in the respective measurement periods τ1 to τ3 are different from each other. Therefore, it is possible to acquire three or more combinations of the artificial magnetic fields $A_x$ and $A_y$, and the spin polarization degrees $M_x$, which are necessary to calculate the original magnetic field vector C ($C_x$, $C_y$, $C_z$) using Equation 17, and having different spin polarization degrees $M_x$.

Example 5

Example 5 is an example in which a predetermined magnetic field is formed in the measurement region 5 instead of bring the measurement region 5 in which a measurement target object is not placed into a zero magnetic field state as in the above Examples. A magnetic field which is desired to be formed in the measurement region 5 in which a measurement target object is not placed is referred to as a target magnetic field. If the target magnetic field is desired to be formed as not a zero magnetic field but a predetermined magnetic field, combinations of the measurement value (the square difference $W_-$) obtained on the basis of a signal output from the magnetic sensor 10 and values of the artificial magnetic field $A_x$ and $A_y$ are acquired in step S03 illustrated in FIG. 13, and then the following process is performed.

As a first procedure, a magnetic field of the measurement region 5 is calculated as the original magnetic field C using the acquired combinations of the acquired measurement value (the square difference $W_-$) and the artificial magnetic field $A_x$ and $A_y$ (corresponding to step S05). Next, as a second procedure, a measurement target object (subject 9) is disposed in the measurement region 5 (corresponding to step S07). In Example 5, since the target magnetic field is formed not as a zero magnetic field but a predetermined magnetic field, applying (step S06 and step S08) the bias magnetic field $B_b$ which cancels out the calculated original magnetic field C to the measurement region 5 is not performed.

Next, as a third procedure, a magnetic field corresponding to a difference between the target magnetic field which is a predetermined magnetic field desired to be formed in the measurement region 5 and the original magnetic field C is generated by the first magnetic field generators 8X, the second magnetic field generators 8Y, and the third magnetic field generators 8Z (corresponding to step S08). Consequently, the artificial magnetic fields A applied by the magnetic field generator 8 (8X, 8Y, and 8Z) and the original magnetic field C are combined with each other, and thus a predetermined magnetic field as the target magnetic field can be formed in the measurement region 5. The order of the second procedure and the third procedure may be changed.

In addition, as a fourth procedure, in a period in which the third procedure is being executed and the second procedure is completed, the magnetic field B generated by the measurement target object is measured using a measurement value (the square difference $W_-$) obtained on the basis of a signal output from the magnetic sensor 10 (corresponding to step S11). Consequently, the magnetic field B generated by the measurement target object can be measured in a state in which the predetermined target magnetic field is formed in the measurement region 5.

Also in the above Examples 1 to 4, a predetermined magnetic field can be formed in the measurement region 5 as the target magnetic field by generating a magnetic field corresponding to a difference between the target magnetic field which is the predetermined magnetic field desired to be formed in the measurement region 5 and the original magnetic field C. In Example 5, if the target magnetic field is set to a zero magnetic field in order to cancel out the original magnetic field C which enters the measurement region 5 from the outside, it is possible to accurately measure the magnetic field B (strictly, a Z direction component of the magnetic field) generated by the measurement target object.

Example 6

Example 6 is an example in which a magnetic field of a predetermined three-dimensional vector is formed as the target magnetic field in the measurement region 5 compared with Example 5. In Example 6, a first procedure and a second procedure are the same as in Example 5.

As a third procedure, the first magnetic field generators 8X generate a constant magnetic field in which an X direction component of a magnetic field corresponding to a difference between the target magnetic field as a predetermined magnetic field formed in the measurement region 5 and the original magnetic field C ($C_x$, $C_y$, $C_z$) is added to the constant magnetic field with the first level on the X side, the second magnetic field generators 8Y generate a magnetic field having a Y direction component of the magnetic field corresponding to the difference, and the third magnetic field generators 8Z generate a magnetic field having a Z direction component of the magnetic field corresponding to the difference (corresponding to step S08). Consequently, the artificial magnetic field A ($A_x$, $A_y$, $A_z$) applied by the magnetic field generator 8 (8X, 8Y, and 8Z) and the original magnetic field C ($C_x$, $C_y$, $C_z$) are combined with each other, and thus a magnetic field of a predetermined three-dimensional vector can be formed as the target magnetic field in the measurement region 5. The order of the second procedure and the third procedure may be changed.

In addition, as a fourth procedure, in a period in which the third procedure is being executed and the second procedure is completed, the magnetic field B ($B_x$, $B_y$, $B_z$) generated by the measurement target object is measured using a measurement value (the square difference $W_-$) obtained on the basis of a signal output from the magnetic sensor 10, a third alternating magnetic field, and a fourth alternating magnetic field (corresponding to step S11). Consequently, the magnetic field B generated by the measurement target object can be measured in a state in which the predetermined target magnetic field of a predetermined three-dimensional vector is formed in the measurement region 5.

Also in the above Examples 1 to 4, a predetermined magnetic field can be formed in the measurement region 5 as the target magnetic field by generating a magnetic field having components in the X, Y and Z directions of a magnetic field corresponding to a difference between the target magnetic field which is the predetermined magnetic field desired to be formed in the measurement region 5 and the original magnetic field C ($C_x$, $C_y$, $C_z$). In Example 6, if the target magnetic field is set to a zero magnetic field in order to cancel out the original magnetic field C ($C_x$, $C_y$, $C_z$) which enters the measurement region 5 from the outside, it is possible to accurately measure the magnetic field B generated by the measurement target object.

Operations and Effects

As described above, according to the magnetic field measurement apparatus 1 of the present embodiment, the gas cell 12 in which a gas of an alkali metal atom or the like is enclosed is irradiated with irradiation light (probe light) in one direction (Z axis direction), and thus it is possible to calculate the magnetic field vector ($C_x$, $C_y$, $C_z$) of the measurement region 5.

Specifically, the magnetic field $A_x$ which is the time function f(t) having the amplitude $A_0$ taking n fixed values $f_i$ (where i=1, . . . , and n), and the magnetic field $A_y$ which is the time function g(t) having the amplitude $A_0$ taking m fixed values $g_j$ (where j=1, . . . , and m) are applied in each of the X axis and Y axis directions perpendicular to an irradiation direction (Z axis direction) of the irradiation light (probe light). In addition, three or more combinations of the artificial magnetic fields $A_x$ and $A_y$, and spin polarization degrees $M_x$ corresponding to a measurement value (square difference $W_-$) on the basis of a signal output from the magnetic sensor 10, and having different spin polarization degrees $M_x$, are acquired. The magnetic field C ($C_x$, $C_y$, $C_z$) is calculated according to Equation 17 using the combinations, the spin polarization degrees $M_x$, and artificial magnetic fields $A_x$ and $A_y$.

Modification Examples

Embodiments to which the invention is applicable are not limited to the above-described embodiment, and the embodiment may be modified as appropriate within the scope without departing from the spirit of the invention.
(A) Bias Magnetic Field $B_b$ In the above-described embodiment, the bias magnetic field $B_b$ which cancels out the original magnetic field C is generated by the magnetic field generator 8, and the magnetic field B ($B_x$, $B_y$, $B_z$) generated by the measurement target object is measured, but measurement is performed without generating the bias magnetic field $B_b$. Specifically, first, in the same manner as in the above-described embodiment, the original magnetic field $C_x$ is measured in a state in which the measurement target object is not placed. Thereafter, the measurement target object is made to be close to the magnetic sensor 10, and a magnetic field generated by the measurement target object is measured, but, at this time, only the artificial magnetic field A is generated by the magnetic field generator 8. In this case, a magnetic field applied to the measurement region 5 is a combined magnetic field of the original magnetic field C, the magnetic field B from the measurement target object, and the artificial magnetic field A generated by the magnetic field generator 8. Therefore, a magnetic field obtained by subtracting the original magnetic field $C_x$ which is measured in advance from the magnetic field $C_x'$ which is calculated using Equation 17 is the magnetic field B generated by the measurement target object.
(B) Measurement Target Object In the above-described embodiment, the measurement target object is the human body, and a magnetic field (heart magnetic field) from the heart or a magnetic field (brain magnetic field) from the brain is measured, but the measurement target object may be other objects. In addition, depending on a measurement target object, instead of causing the measurement target object to be close to the magnetic sensor 10 as in the above-described embodiment, the magnetic sensor 10 may be caused to be close to the measurement target object, and a magnetic field generated by the measurement target object may be measured.

The entire disclosure of Japanese Patent Applications No.2014-243867, filed Dec. 2, 2014 and No.2015-158756, filed Aug. 11, 2015 are expressly incorporated by reference herein.

What is claimed is:

1. A magnetic field measurement apparatus in which a first direction, a second direction, and a third direction are perpendicular to each other, the apparatus comprising:
   a light source that emits light;
   a medium through which the light passes in the third direction and that changes optical characteristics depending on a magnetic field of the measurement region;
   a photodetector that detects the optical characteristics;
   a second magnetic field generator that applies a magnetic field in the second direction to the measurement region; and
   a calculation controller that causes the second magnetic field generator to generate a constant magnetic field with a first level on the second direction side, a constant magnetic field with a second level on the second direction side, and a constant magnetic field with a third level on the second direction side, as the magnetic field in the second direction, and calculates the magnetic field of the measurement region using a detection result from the photodetector and the magnetic field in the second direction.

* * * * *